(12) United States Patent
Tracey et al.

(10) Patent No.: US 8,729,129 B2
(45) Date of Patent: May 20, 2014

(54) NEURAL TOURNIQUET

(75) Inventors: Kevin J. Tracey, Old Greenwich, CT (US); Carol Ann Amella, East Northport, NY (US); Christopher Czura, Lake Grove, NY (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 464 days.

(21) Appl. No.: 11/088,683

(22) Filed: Mar. 24, 2005

(65) Prior Publication Data

US 2005/0282906 A1    Dec. 22, 2005

Related U.S. Application Data

(60) Provisional application No. 60/556,096, filed on Mar. 25, 2004.

(51) Int. Cl.
*A61K 31/4747* (2006.01)
*A61K 31/4439* (2006.01)
*A61K 31/165* (2006.01)

(52) U.S. Cl.
USPC ............ 514/614; 514/278; 514/343; 600/13; 600/37

(58) Field of Classification Search
None
See application file for complete search history.

(56) References Cited

U.S. PATENT DOCUMENTS

| | | | |
|---|---|---|---|
| 2,164,121 A | 6/1939 | Pescador | |
| 3,363,623 A | 1/1968 | Atwell | |
| 4,073,296 A | 2/1978 | McCall | |
| 4,098,277 A | 7/1978 | Mendell | |
| 4,305,402 A | 12/1981 | Katims | |
| 4,503,863 A | 3/1985 | Katims | |
| 4,573,481 A | 3/1986 | Bullara | |
| 4,590,946 A | 5/1986 | Loeb | |
| 4,632,095 A | 12/1986 | Libin | |
| 4,649,936 A | 3/1987 | Ungar et al. | |
| 4,702,254 A | 10/1987 | Zabara | |
| 4,840,793 A | 6/1989 | Todd, III et al. | |
| 4,867,164 A | 9/1989 | Zabara | |
| 4,929,734 A | 5/1990 | Coughenour et al. | |
| 4,935,234 A | 6/1990 | Todd, III et al. | |
| 4,979,511 A | 12/1990 | Terry, Jr. | |
| 4,991,578 A | 2/1991 | Cohen | |
| 5,019,648 A | 5/1991 | Schlossman et al. | |
| 5,025,807 A | 6/1991 | Zabara | |
| 5,038,781 A | 8/1991 | Lynch | |
| 5,049,659 A | 9/1991 | Cantor et al. | |
| 5,073,560 A | 12/1991 | Wu et al. | |
| 5,106,853 A | 4/1992 | Showell et al. | |
| 5,111,815 A | 5/1992 | Mower | |
| 5,154,172 A | 10/1992 | Terry, Jr. et al. | |
| 5,175,166 A | 12/1992 | Dunbar et al. | |
| 5,179,950 A | 1/1993 | Stanislaw | |
| 5,186,170 A | 2/1993 | Varrichio et al. | |
| 5,188,104 A | 2/1993 | Wernicke et al. | |
| 5,203,326 A | 4/1993 | Collins | |
| 5,205,285 A | 4/1993 | Baker, Jr. | |
| 5,215,086 A | 6/1993 | Terry, Jr. et al. | |
| 5,215,089 A | 6/1993 | Baker, Jr. | |
| 5,222,494 A | 6/1993 | Baker, Jr. | |
| 5,231,988 A | 8/1993 | Wernicke et al. | |
| 5,235,980 A | 8/1993 | Varrichio et al. | |
| 5,237,991 A | 8/1993 | Baker et al. | |
| 5,251,634 A | 10/1993 | Weinberg | |
| 5,263,480 A | 11/1993 | Wernicke et al. | |
| 5,269,303 A | 12/1993 | Wernicke et al. | |
| 5,299,569 A | 4/1994 | Wernicke et al. | |
| 5,304,206 A | 4/1994 | Baker, Jr. et al. | |
| 5,330,507 A | 7/1994 | Schwartz | |
| 5,330,515 A | 7/1994 | Rutecki et al. | |
| 5,335,657 A | 8/1994 | Terry, Jr. et al. | |
| 5,344,438 A | 9/1994 | Testerman et al. | |
| 5,351,394 A | 10/1994 | Weinberg | |
| 5,403,845 A | 4/1995 | Dunbar et al. | |
| 5,458,625 A | 10/1995 | Kendall | |
| 5,472,841 A | 12/1995 | Jayasena et al. | |
| 5,487,756 A | 1/1996 | Kallesoe et al. | |
| 5,496,938 A | 3/1996 | Gold et al. | |
| 5,503,978 A | 4/1996 | Schneider et al. | |
| 5,531,778 A | 7/1996 | Maschino et al. | |
| 5,540,730 A | 7/1996 | Terry, Jr. et al. | |
| 5,540,734 A | 7/1996 | Zabara | |
| 5,567,588 A | 10/1996 | Gold et al. | |
| 5,567,724 A | 10/1996 | Kelleher et al. | |
| 5,571,150 A * | 11/1996 | Wernicke et al. ............... 607/72 |

(Continued)

FOREIGN PATENT DOCUMENTS

DE    2628045 A1    1/1977
DE    3736664 A1    5/1989

(Continued)

OTHER PUBLICATIONS

Shapiro et al (Thromb Haemost 80 (1998) 773-8).*
Abraham, E. "Coagulation Abnormalities in Acute Lung Injury and Sepsis," *Am. J. Respir. Cell Mol. Biol.*, 22: 401-404 (2000).
Bernick, T. R., et al., "Pharmacological Stimulaton of the Cholinergic Antiinflammatory Pathway." *J. Exp. Med.*, 195(6): 781-788 (2002).
Boldyreff, W. N., "Gastric and intestinal mucus, its properties and physiological importance," *Acta Medica Scandinavica (journal)*, 89:1-14 (1936).

(Continued)

*Primary Examiner* — Frederick Krass
*Assistant Examiner* — Celeste A Roney
(74) *Attorney, Agent, or Firm* — Shay Glenn LLP

(57) ABSTRACT

Disclosed is a method of reducing bleed time in a subject by activation of the cholinergic anti-inflammatory pathway in said subject. The cholinergic anti-inflammatory pathway can be activated by direct or indirect stimulation of the vagus nerve. The cholinergic anti-inflammatory pathway can also be activated by administering an effective amount of cholinergic agonist or acetylcholinesterase inhibitor to the subject.

24 Claims, 4 Drawing Sheets

(56) References Cited

U.S. PATENT DOCUMENTS

| | | | |
|---|---|---|---|
| 5,580,737 A | 12/1996 | Polisky et al. |
| 5,582,981 A | 12/1996 | Toole et al. |
| 5,604,231 A | 2/1997 | Smith et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Lino et al. |
| 5,712,375 A | 1/1998 | Jensen et al. |
| 5,718,912 A | 2/1998 | Thomspon et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A * | 12/1999 | Hill et al. ................... 607/9 |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie et al. |
| 6,147,204 A | 11/2000 | Gold et al. |
| 6,159,145 A | 12/2000 | Satoh |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,475 B1 | 5/2004 | Whitehurst et al. |
| 6,760,626 B1 | 7/2004 | Boveja |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,544,497 B2 | 6/2009 | Sinclair et al. |

(56) References Cited

U.S. PATENT DOCUMENTS

| | | |
|---|---|---|
| 7,561,918 B2 | 7/2009 | Armstrong et al. |
| 7,711,432 B2 | 5/2010 | Thimineur et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,937,145 B2 | 5/2011 | Dobak |
| 2001/0002441 A1 | 5/2001 | Boveja |
| 2002/0026141 A1 | 2/2002 | Houben et al. |
| 2002/0040035 A1 | 4/2002 | Meyers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0099418 A1* | 7/2002 | Naritoku et al. .............. 607/45 |
| 2002/0138075 A1 | 9/2002 | Edwards et al. |
| 2002/0138109 A1 | 9/2002 | Keogh et al. |
| 2002/0198570 A1 | 12/2002 | Puskas |
| 2003/0018367 A1 | 1/2003 | DiLorenzo |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0015202 A1 | 1/2004 | Chandler et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0125044 A1 | 6/2005 | Tracey |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |
| 2006/0142802 A1 | 6/2006 | Armstrong |
| 2006/0142822 A1 | 6/2006 | Tulgar |
| 2006/0149337 A1 | 7/2006 | John |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178703 A1 | 8/2006 | Huston et al. |
| 2006/0178706 A1 | 8/2006 | Lisogurski et al. |
| 2006/0190044 A1 | 8/2006 | Libbus et al. |

(56) References Cited

U.S. PATENT DOCUMENTS

| | | |
|---|---|---|
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0259077 A1 | 11/2006 | Pardo et al. |
| 2006/0271115 A1 | 11/2006 | Ben-Ezra et al. |
| 2006/0287678 A1 | 12/2006 | Shafer |
| 2006/0287679 A1 | 12/2006 | Stone |
| 2006/0293723 A1 | 12/2006 | Whitehurst et al. |
| 2007/0055324 A1 | 3/2007 | Thompson et al. |
| 2007/0067004 A1 | 3/2007 | Boveja et al. |
| 2007/0093434 A1 | 4/2007 | Rossetti et al. |
| 2007/0100380 A1 | 5/2007 | Fukui |
| 2007/0118178 A1 | 5/2007 | Fukui |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0142870 A1 | 6/2007 | Knudson et al. |
| 2007/0142874 A1 | 6/2007 | John |
| 2007/0150021 A1 | 6/2007 | Chen et al. |
| 2007/0250145 A1 | 10/2007 | Kraus et al. |
| 2008/0140138 A1 | 6/2008 | Ivanova et al. |
| 2008/0208266 A1 | 8/2008 | Lesser et al. |
| 2008/0234790 A1 | 9/2008 | Bayer et al. |
| 2008/0249439 A1 | 10/2008 | Tracey et al. |
| 2009/0048194 A1 | 2/2009 | Aerssens et al. |
| 2010/0241183 A1 | 9/2010 | DiLorenzo |
| 2010/0249859 A1 | 9/2010 | DiLorenzo |
| 2010/0312320 A1 | 12/2010 | Faltys et al. |
| 2011/0054569 A1 | 3/2011 | Zitnik et al. |
| 2011/0106208 A1 | 5/2011 | Faltys et al. |
| 2012/0290035 A1 | 11/2012 | Levine et al. |

FOREIGN PATENT DOCUMENTS

| | | |
|---|---|---|
| DE | 20316509 U1 | 4/2004 |
| GB | 04133 | 2/1910 |
| WO | WO93/01862 A1 | 2/1993 |
| WO | WO 97/30998 | 8/1997 |
| WO | WO98/20868 A1 | 5/1998 |
| WO | WO00/27381 A2 | 5/2000 |
| WO | WO00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO 02/44176 A1 | 6/2002 |
| WO | WO 02/057275 A1 | 7/2002 |
| WO | WO 03/072135 A | 9/2003 |
| WO | WO2004/000413 A2 | 12/2003 |
| WO | WO2004/064918 A1 | 8/2004 |
| WO | WO2006/073484 A1 | 7/2006 |

OTHER PUBLICATIONS

Doshi, S. N., and Marmur, J. D., "Evolving role of tissue factor and its pathway inhibitor," Crit. Care Med., 30(5 Suppl): S241-S250 (2002).

Esmon, C., "The protein C pathway," Crit. Care Med., 28(9 Suppl): S44-S48 (2000).

Holladay, M. W., et al., "Neuronal Nicotinic Acetylcholine Receptors as Targets for Drug Discovery," Journal of Medicinal Chemistry, 40(26):4169-4194 (1997).

Stalcup, S. A., et al., "Endothelial Cell Functions in the Hemodynamic Responses to Stress," Annals of the New York Academy of Sciences, 401: 117-131 (1982).

Tracey, K. J., "The inflammatory reflex," Nature, 420: 853-859 (2002).

Vanhoutte, P. M., and Shephard, J. T., "Muscarinic and beta-adrenergic prejunctional modulation of adrenergic neurotransmission in the blood vessel wall," Gen. Pharmac. 14:35-37 (1983).

von Känel, R., et al., "Effects of nonspecific β-adrenergic stimulation and blockade on blood coagulation in hypertension," J. Appl. Physiol., 94: 1455-1459 (2003).

US 6,184,239, 02/2001, Puskas et al. (Withdrawn).

Tracey et al.; U.S. Appl. No. 12/109,334 entitled "Inhibition of inflammatory cytokine production by cholinergic agonists and vagus nerve stimulation," filed Apr. 24, 2008.

Tracey et al.; U.S. Appl. No. 12/198,808 entitled "Devices and methods for inhibiting granulocyte activation by neural stimulation," filed Aug. 26, 2008.

Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.

Antonica, A., et al., Vagal control of lymphocyte release from rat thymus, J. Auton. Nerv. Syst., vol. 48, pp. 187-197, 1994.

Asakura et al., Non-surgical therapy for ulcerative colitis, Nippon Geka Gakkai Zasshi, vol. 98, No. 4, pp. 431-437, Apr. 1997 (abstract only).

Bernik et al., Vagus nerve stimulation attenuates endotoxic shock and cardiac TNF production, 87th Clinical Congress of the American College of Surgeons, New Orleans, LA, Oct. 9, 2001.

Bernik et al., Vagus nerve stimulation attenuates LPS-induced cardiac TNF production and myocardial depression in shock, New York Surgical Society, New York, NY, Apr. 11, 2001.

Bhattacharya, S.K. et al., Central muscarinic receptor subtypes and carrageenin-induced paw oedema in rats, Res. Esp. Med. vol. 191, pp. 65-76, 1991.

Bianchi et al., Suppression of proinflammatory cytokines in monocytes by a tetravalent guanylhydrazone, Journal of Experimental Medicine, vol. 183, pp. 927-936, Mar. 1996.

Blum, A. et al., Role of cytokines in heart failure, Am. Heart J., vol. 135, pp. 181-186, 1998.

Borovikova et al., Efferent vagus nerve activity attenuates cytokine-mediated inflammation, Society for Neuroscience Abstracts, vol. 26, No. 102, 2000 (abstract only).

Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.

Borovikova et al., Role of the efferent vagus nerve signaling in the regulation of the innate immune response to LPS, (supplemental to Shock, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.

Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).

Borovikova et al., Vagotomy blocks the protective effects of I.C.V. CNI-1493 against LPS-induced Shock, (Supplemental to Shock, vol. 11, 1999, Molecular, cellular, and systemic pathobioloigal aspects and therapeutic approaches, abstacts and program, Fourth International Shock Congress and 22nd Annual Conference on Shock, Philadelphia, PA, Jun. 12-16, 1999), Abstract No. 277.

Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.

Borovikova, L. V., et al., Vagus nerve stimulation attenuates the systemic inflammatory response to endotoxin, Nature, vol. 405, No. 6785: pp. 458-462, May 25, 2000.

Bumgardner, G. L. et al., Transplantation and cytokines, Seminars in Liver Disease, vol. 19, No. 2, pp. 189-204, 1999.

Carteron, N. L., Cytokines in rheumatoid arthritis: trials and tribulations, Mol. Med. Today, vol. 6, pp. 315-323, 2000.

Dibbs, Z., et al., Cytokines in heart failure: pathogenetic mechanisms and potential treatment, Proc. Assoc. Am. Physicians, vol. 111, No. 5, pp. 423-428, 1999.

Dinarello, C. A., The interleukin-1 family: 10 years of discovery, FASEB J., vol. 8, No. 15, pp. 1314-1325, 1994.

Fleshner, M., et al., Thermogenic and corticosterone responses to intravenous cytokines (IL-1? and TNF-?) are attenuated by subdiaphragmatic vagotomy, J. Neuroimmunol., vol. 86, pp. 134-141, 1998.

(56) References Cited

OTHER PUBLICATIONS

Fox, et al., Use of muscarinic agonists in the treatment of Sjorgren' syndrome, Clin. Immunol., vol. 101, No. 3; pp. 249-263, 2001.
Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, 2000.
Gracie, J. A., et al., A proinflammatory role for IL-18 in rheumatoid arthritis, J. Clin. Invest., vol. 104, No. 10, pp. 1393-1401, 1999.
Granert et al., Suppression of macrophage activation with CNI-1493 increases survival in infant rats with systemic haemophilus influenzae infection, Infection and Immunity, vol. 68, No. 9, pp. 5329-5334, Sep. 2000.
Hirano, T., Cytokine suppresive agent improves survival rate in rats with acute pancreatitis of closed duodenal loop, J. Surg. Res., vol. 81, No. 2, pp. 224-229, 1999.
Hommes, D. W. et al., Anti- and Pro-inflammatory cytokines in the pathogenesis of tissue damage in Crohn's disease, Current Opinion in Clinical Nutrition and Metabolic Care, vol. 3., pp. 191-195, 2000.
Hsu, H. Y., et al., Cytokine release of peripheral blood monoculear cells in children with chronic hepatitis B virus infection, J. Pediatr. Gastroenterol., vol. 29, No. 5, pp. 540-545, 1999.
Hu, et al., The effect of norepinephrine on endotoxin-mediated macrophage activation, J. Neuroimmunol., vol. 31, pp. 35-42, 1991.
Jander, S. et al., Interleukin-18 is induced in acute inflammatory demyelinating polymeuropathy, J. Neuroimmunol., vol. 114, pp. 253-258, 2001.
Kanai, T. et al., Interleukin-18 and Crohn's disease, Digestion, vol. 63, suppl. 1, pp. 37-42, 2001.
Katagiri, M., et al., Increased cytokine production by gastric mucosa in patients with *Helicobacter pylori* infection, J. Clin, Gastroenterol., vol. 25, Suppl. 1, pp. S211-S214, 1997.
Kimball, et al., Levamisole causes differential cytokine expression by elicited mouse peritoneal macrophases, Journal of Leukocyte Biology, vo. 52, No. 3, pp. 349-356, 1992 (abstract only).
Kimmings, A. N., et al., Systemic inflammatory response in acute cholangitis and after subsequent treatment, Eur. J. Surg., vol. 166, pp. 700-705, 2000.
Kirchner et al.; Left vagus nerve stimulation suppresses experimentally induced pain; Neurology; vol. 55; pp. 1167-1171; 2000.
Kumins, N. H., et al., Partial hepatectomy reduces the endotoxin-induced peak circulating level of tumor necrosis factor in rats, Shock, vol. 5, No. 5, pp. 385-388, 1996.
Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, 1995.
Lipton, J. M. et al.; Anti-inflammatory actions of the neuroimmunomodulator ?-MSH, Immunol. Today, vol. 18, pp. 140-145, 1997.
Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.
McGuinness, P. H., et al., Increases in intrahepatic CD68 positive cells, MAC387 positive cells, and proinflammatory cytokines (particulary interleukin 18) in chronic hepatitis C infection, Gut, vol. 46, pp. 260-269, 2000.
Minnich et al.; Anti-cytokine and anti-inflammatory therapies for the treatment of severe sepsis: progress and pitfalls; Proceedings of the Nutrition Society; vol. 63; pp. 437-441; 2004.
Molina et al., CNI-1493 attenuates hemodynamic and pro-inflammatory responses to LPS, Shock, vol. 10, No. 5, pp. 329-334, Nov. 1998.
Nathan, C. F., Secretory products of macrophages, J. Clin. Invest., vol. 79, pp. 319-326, 1987.
Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; 2001.

Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.
Prystowsky, J. B. et al., Interleukin-1 mediates guinea pig gallbladder inflammation in vivo, J. Surg. Res., vol. 71, No. 2, pp. 123-126, 1997.
Pulkki, K. J., Cytokines and cardiomyocyte death, Ann. Med., vol. 29, pp. 339-343, 1997.
Rayner, S. A. et al., Local bioactive tumour necrosis factor (TNF) in corneal allotransplantation, Clin. Exp. Immunol., vol. 122, pp. 109-116, 2000.
Romanovsky, A. A., et al.,The vagus nerve in the thermoregulatory response to systemic inflammation, Am. J. Physiol., vol. 273, No. 1 (part 2), pp. R407-R413, 1997.
Scheinman, R. I., et al., Role of transcriptional activation of I?B? in mediation of immunosuppression by glucocorticoids, Science, vol. 270, pp. 283-286, 1995.
Sugano et al., Nicotine inhibits the production of inflammatory mediators in U937 cells through modulation of nuclear factor-kappaβ activation, Biochemical and Biophysical Research Communications, vol. 252, No. 1, pp. 25-28, Nov. 9, 1998.
Tracey et al., Mind over immunity, Faseb Journal, vol. 15, No. 9, pp. 1575-1576, Jul. 2001.
Tracey, K. J. et al., Shock and tissue injury induced by recombinant human cachectin, Science, vol. 234, pp. 470-474, 1986.
Ventureyra, Transcutaneous vagus nerve stimulation for partial onset seizure therapy, Child's Nerv Syst, vol. 16, pp. 101-102, 2000.
Villa et al., Protection against lethal polymicrobial sepsis by CNI-1493, an inhibitor of pro-inflammatory cytokine synthesis, Journal of Endotoxin Research, vol. 4, No. 3, pp. 197-204, 1997.
Waserman, S. et al., TNF-? dysregulation in asthma: relationship to ongoing corticosteroid therapy, Can. Respir. J., vol. 7, No. 3, pp. 229-237, 2000.
Watanabe, H. et al., The significance of tumor necrosis factor (TNF) levels for rejection of joint allograft, J. Reconstr. Microsurg., vol. 13, No. 3, pp. 193-197, 1997.
Watkins, L.R. et al., Implications of immune-to-brain communication for sickness and pain, Proc. Natl. Acad. Sci. U.S.A., vol. 96, pp. 7710-7713, 1999.
Woiciechowsky, C. et al., Sympathetic activation triggers systemic interleukin-10 release in immunodepression induced by brain injury, Nature Med., vol. 4, No. 7, pp. 808-813, 1998.
Yeh, S.S. et al., Geriatric cachexia: the role of cytokines, Am. J. Clin. Nutr., vol. 70, pp. 183-197, 1999.
Zhang et al., Tumor necrosis factor, The Cytokine Handbook, 3rd ed., Ed. Thompson, Academic Press, pp. 517-548, 1998.
Ilton et al., "Differential expression of neutrophil adhesion molecules during coronary artery surgery with cardiopulmonary bypass" Journal of Thoracic and Cardiovascular Surgery, Mosby-Year Book, inc., St. Louis, Mo, US, pp. 930-937, Nov. 1, 1999.
Shapiro et al.; Prospective, randomised trial of two doses of rFVIIa (NovoSeven) in haemophilia patients with inhibitors undergoing surgery; Thromb Haemost; vol. 80; pp. 773-778; 1998.
Huston et al.; U.S. Appl. No. 12/259,208 entitled "Treating inflammatory disorders by stimulation of the cholinergic anti-inflammatory pathway," filed Oct. 27, 2008.
Saghizadeh et al.; The expression of TNFα by human muscle; J. Clin. Invest.; vol. 97; No. 4; pp. 1111-1116; 1996.
Benthem et al.; Parasympathetic inhibition of sympathetic neural activity to the pancreas; Am.J.Physiol Endocrinol.Metab; 280; pp. E378-E381; 2001.
Bernik et al., Vagus nerve stimulation attenuates cardiac TNF production in endotoxic shock, (supplemental to Shock, vol. 15, 2001, Injury, inflammation and sepsis: laboratory and clinical approaches, Shock, Abstracts, 24th Annual Conference on Shock, Marco Island, FL, Jun. 9-12, 2001), Abstract No. 81.
Besedovsky, H., et al., Immunoregulatory feedback between interleukin-1 and glucocorticoid hormones, Science, vol. 233, pp. 652-654, 1986.
Blackwell, T. S. et al., Sepsis and cytokines: current status, Br. J. Anaesth., vol. 77, pp. 110-117, 1996.

(56) References Cited

OTHER PUBLICATIONS

Borovikova et al., Acetylcholine inhibition of immune response to bacterial endotoxin in human macrophages, Abstracts, Society for Neuroscience, 29th Annual Meeting, Miami Beach, FL, Oct. 23-28, 1999, Abstract No. 624.6.

Bulloch et al.; Characterization of choline O-acetyltransferase (ChAT) in the BALB/C mouse spleen; Int.J.Neurosci.; 76; pp. 141-149; 1994.

Burke et al., Bent pseudoknots and novel RNA inhibitors of type 1 human immunodeficiency virus (HIV-1) reverse transcriptase, J. Mol. Biol., vol. 264; pp. 650-666, 1996.

Cano et al.; Characterization of the central nervous system innervation of the rat spleen using viral transneuronal tracing; J.Comp Neurol.; 439; pp. 1-18; 2001.

DAS, Critical advances in spticemia and septic shock, Critical Care, vol. 4, pp. 290-296, Sep. 7, 2000.

Del Signore et al; Nicotinic acetylcholine receptor subtypes in the rat sympathetic ganglion: pharmacological characterization, subcellular distribution and effect of pre- and postganglionic nerve crush; J.Neuropathol.Exp.Neurol.; 63(2); pp. 138-150; Feb. 2004.

Ellington et al., In vitro selection of RNA molecules that bind specific ligands, Nature, vol. 346, pp. 818-822, Aug. 30, 1990.

Fox, D. A., Cytokine blockade as a new strategy to treat rheumatoid arthritis, Arch. Intern. Med., vol. 160, pp. 437-444, Feb. 28, 2000.

Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, 1995.

Ghelardini et al., S-(−)-ET 126: A potent and selective M1 antagonist in vitro and in vivo, Life Sciences, vol. 58, No. 12, pp. 991-1000, 1996.

Goyal et al., Nature of the vagal inhibitory innervation to the lower esophageal sphincter, Journal of Clinical Investigation, vol. 55, pp. 1119-1126, May 1975.

Green et al., Feedback technique for deep relaxation, Psycophysiology, vol. 6, No. 3, pp. 371-377, Nov. 1969.

Gregory et al., Neutrophil-kupffer-cell interaction in host defenses to systemic infections, Immunology Today, vol. 19, No. 11, pp. 507-510, Nov. 1998.

Guslandi, M., Nicotine treatment for ulcerative colitis, Br. J. Clin. Pharmacol., vol. 48, pp. 481-484, 1999.

Harrison's Principles of Internal Medicine, vol. 13, pp. 511-515 and 1433-1435, 1994.

Hirao et al., The limits of specificity: an experimental analysis with RNA aptamers to MS2 coat protein variants, Mol. Divers., vol. 4, pp. 75-89, 1999.

Hsu, et al., Analysis of efficiency of magnetic stimulation, IEEE Trans. Biomed. Eng., vol. 50(11), pp. 1276-1285, Nov. 2003.

Jaeger et al., The structure of HIV-1 reverse transcriptase complexed with an RNA pseudoknot inhibitor, The EMBO Journal, 17(15), pp. 4535-4542, 1998.

Joshi et al., Potent inhibition of human immunodeficiency virus type 1 replection by template analog reverse transcriptase, J. Virol., 76(13), pp. 6545-6557, Jul. 2002.

Kawashima, et al., Extraneuronal cholinergic system in lymphocytes, Pharmacology & Therapeutics, vol. 86, pp. 29-48, 2000.

Kees et al; Via beta-adrenoceptors, stimulation of extrasplenic sympathetic nerve fibers inhibits lipopolysaccharide-induced TNF secretion in perfused rat spleen; J.Neuroimmunol.; 145; pp. 77-85; 2003.

Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.

Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.

LeNovere, N. et al., Molecular evolution of the nicotinic acetylcholine receptor: an example of multigene family in excitable cells, J. Mol. Evol., 40, pp. 155-172, 1995.

Leonard, S. et al., Neuronal nicotinic receptors: from structure to function, Nicotine & Tobacco Res. 3:203-223 (2001).

Madretsma, G. S, et al., Nicotine inhibits the in vitro production of interleukin 2 and tumour necrosis factor-alpha by human monocucleur cells, Immunopharmacology, vol. 35, No. 1, pp. 47-51, 1996.

Nagashima et al., Thrombin-activatable fibrinolysis inhibitor (TAFI) deficiency is compatible with murine life, J. Clin. Invest., 109, pp. 101-110, 2002.

Noguchi et al., Increases in Gastric acidity in response to electroacupuncture stimulation of hindlimb of anesthetized rats, Jpn. J. Physiol., 46(1), pp. 53-58, 1996.

Norton, Can ultrasound be used to stimulate nerve tissue, BioMedical Engineering, 2(1), pp. 6, 2003.

Rinner et al.; Rat lymphocytes produce and secrete acetylcholine in dependence of differentiation and activation; J.Neuroimmunol.; 81; pp. 31-37; 1998.

Saindon et al.; Effect of cervical vagotomy on sympathetic nerve responses to peripheral interleukin-1beta; Auton.Neuroscience Basic and Clinical; 87; pp. 243-248; 2001.

Saito, Involvement of muscarinic M1 receptor in the central pathway of the serotonin-induced bezold jarisch reflex in rats, J. Autonomic Nervous System, vol. 49, pp. 61-68, 1994.

Sandborn, W. J., et al., Transdermal nicotine for mildly to moderately active ulcerative colitis, Ann. Intern. Med, vol. 126, No. 5, pp. 364-371, 1997.

Sato, E., et al., Acetylcholine stimulates alveolar macrophages to release inflammatory cell chemotactic activity, Am. J. Physiol., vol. 274, pp. L970-L979, 1998.

Sato, K.Z., et al., Diversity of mRNA expression for muscarinic acetylcholine receptor subtypes and neuronal nicotinic acetylcholine receptor subunits in human mononuclear leukosytes and leukemic cell lines, Neuroscience Letters, vol. 266, pp. 17-20, 1999.

Schneider et al., High-affinity ssDNA inhibitors of the review transcriptase of type 1 human immunodeficiency virus, Biochemistry, 34(29), pp. 9599-9610, 1995.

Shafer, Genotypic testing for human immunodeficiency virus type 1 drug resistance, Clinical Microbiology Reviews, vol. 15, pp. 247-277, 2002.

Sher, M. E., et al., The influence of cigarette smoking on cytokine levels in patients with inflammatory bowel disease, Inflamm. Bowel Dis., vol. 5, No. 2, pp. 73-78, 1999.

Snyder et al., Correction of hemophilia B in canine and murine models using recombinant adeno-associated viral vectors; Nature Medicine, 5(1), pp. 64-70, Jan. 1999.

Steinlein, New functions for nicotine acetylcholine receptors?, Behavioural Brain Res., vol. 95, pp. 31-35, 1998.

Sternberg, E. M., Perspectives series: cytokines and the brain 'neural-immune interactions in health and disease,' J. Clin. Invest., vol. 100, No. 22, pp. 2641-2647, Dec. 1997.

Sykes, et al., An investigation into the effect and mechanisms of action of nicotine in inflammatory bowel disease, Inflamm. Res., vol. 49, pp. 311-319, 2000.

Toyabe, et al., Identification of nicotinic acetylcholine receptors on lymphocytes in the periphery as well as thymus in mice, Immunology, vol. 92, pp. 201-205, 1997.

Tracey, K. J. et al., Anti-cachectin/TNF monoclonal antibodies prevent septic shock during lethal bacteraemia; Nature, 330: pp. 662-664, 1987.

Tsutsui, H., et al., Pathophysiolocical roles of interleukin-18 in inflammatory liver diseases; Immunol. Rev., 174:192-209, 2000.

Tuerk et al., RNA pseudoknots that inhibit human immunodeficiency virus type 1 reverse transcriptase; Proc. Natl. Acad. Sci. USA, 89, pp. 6988-6992, Aug. 1992.

Tuerk et al., Systematic evolution of ligands by exponential enrichment: RNA ligands to bacteriophage T4 DNA polymerase; Science, 249(4968), pp. 505-510, Aug. 3, 1990.

Van Dijk, A. P., et al., Transdermal nictotine inhibits interleukin 2 synthesis by mononuclear cells derived from healthy volunteers, Eur. J. Clin. Invest, vol. 28, pp. 664-671, 1998.

Walland et al., Compensation of muscarinic brochial effects of talsaclidine by concomitant sympathetic activation in guinea pigs; European Journal of Pharmacology, vol. 330, pp. 213-219, 1997.

(56) References Cited

OTHER PUBLICATIONS

Wang et al; Nicotinic acetylcholine receptor alpha7 subunit is an essential regulator of inflammation; Nature; 421; 384-388; Jan. 23, 2003.
Wang, H., et al., HMG-1 as a late mediator of endotoxin lethality in mice, Science, vol. 285, pp. 248-251, Jul. 9, 1999.
Wathey, J.C. et al., Numerical reconstruction of the quantal event at nicotinic synapses; Biophys. J., vol. 27: pp. 145-164, Jul. 1979.
Watkins, L.R. et al., Blockade of interleukin-1 induced hyperthermia by subdiaphragmatic vagotomy: evidence for vagal mediation of immune-brain communication, Neurosci. Lett., vol. 183, pp. 27-31, 1995.
Whaley, K. et al., C2 synthesis by human monocytes is modulated by a nicotinic cholinergic receptor, Nature, vol. 293, pp. 580-582, Oct. 15, 1981.
Tracey et al.; U.S. Appl. No. 12/415,671 entitled "Methods and systems for reducing inflammation by neuromodulation of T-cell activity," filed Mar. 31, 2009.
Faltys et al.; U.S. Appl. No. 12/434,462 entitled "Vagus nerve stimulation electrodes and methods of use," filed May 1, 2009.
Cicala et al., "Linkage between inflammation and coagulation: An update on the molecular basis of the crosstalk," Life Sciences, vol. 62(20); pp. 1817-1824, 1998.
Kalishevskaya et al. "The character of vagotomy-and atropin-induced hypercoagulation," Fizio. Zh SSSR Im I M Sechenova, 65(3): pp. 398-404, 1979.
Khatun, S., et al., "Induction of hypercoagulability condition by chronic localized cold stress in rabbits," Thromb. and Haemost., 81: pp. 449-455, 1999.
Kudrjashov, et al. "Reflex nature of the physiological anticoagulating system," Nature, vol. 196(4855): pp. 647-649; 1962.
Kuznik, et al., "Secretion of blood coagulation factors into saliva under conditions of hypo-and hypercoagulation," Voprosy Meditsinskoi Khimii, vol. 19(1): pp. 54-57; 1973.
Kuznik, et al., "Heart as an efferent regulator of the process of blood coagulation, and fibrinolysis," Kardiologiia, vol. 13(3): pp. 10-17, 1973.
Kuznik, et al., "Blood Coagulation in stimulation of the vagus nerve in cats," Biull. Eskp. Biol. Med., vol. 78(7): pp. 7-9, 1974.
Kuznik, et al., "The role of the vascular wall in the mechanism of control of blood coagulation and fibrinolysis on stimulation of the vagus nerve," Cor Vasa, vol. 17(2): pp. 151-158, 1975.
Kuznik, et al., "The dynamics of procoagulatible and fibrinolytic activities during electrical stimulation of peripheral nerves," Fizio. Zh SSSR Im I M Sechenova, 3: pp. 414-420, 1979.
Lang, et al., "Neurogienic control of cerebral blood flow," Experimental Neurology, 43: pp. 143-161, 1974.
Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, 1974.
Mishchenko, et al., "Coagulation of the blood and fibrinolysos in dogs during vagal stimulation," Fizio. Zh SSSR Im I M Sechenova, vol. 61(1): pp. 101-107, 1975.
Von Känal, et al., Effects of sympathetic activation by adrenergic infusions on hemostasis in vivo, Eur. J. Haematol., vol. 65: pp. 357-369, 2000.
Cohen, "The immunopathogenesis of sepsis," vol. 420(19): pp. 885-891, 2002.
Weiner, et al., "Inflammation and therapeutic vaccination in CNS diseases," vol. 420(19): pp. 879-884, 2002.
Benoist, et al., "Mast cells in autoimmune disease" vol. 420(19): pp. 875-878, 2002.
Faltys, Michael; U.S. Appl. No. 12/620,413 entitled "Devices and methods for optimizing electrode placement for anti-inflamatory stimulation," filed Nov. 17, 2009.
Martindale: The extrapharcopoeia; 28th Ed. London; The pharmaceutical press; pp. 446-485; 1982.
Shi et al.; Effects of efferent vagus nerve excitation on inflammatory response in heart tissue in rats with endotoxemia; vol. 15, No. 1; pp. 26-28; 2003 (Eng. Abstract).
Beliavskaia et al.,"On the effects of prolonged stimulation of the peripheral segment of the vagus nerve . . . ," Fiziologicheskii Zhurnal SSSR Imeni I.M. Sechenova., vol. 52(11); p. 1315-1321, Nov. 1966.
Ben-Noun et al.; Neck circumference as a simple screening measure for identifying overweight and obese patients; Obesity Research; vol. 9; No. 8; pp. 470-477; Aug. 8, 2001.
Bushby et al; Centiles for adult head circumference; Archives of Disease in Childhood; vol. 67; pp. 1286-1287; 1992.
Corcoran, et al., The effects of vagus nerve stimulation on pro- and anti-inflammatory cytokines in humans: a preliminary report, NeuroImmunoModulation, vol. 12, pp. 307-309, 2005.
Hoffer et al.; Implantable electrical and mechanical interfaces with nerve and muscle; Annals of Biomedical Engineering; vol. 8; pp. 351-360; 1980.
Kalishevskaya et al.; Neural regulation of the fluid state of the blood; Usp. Fiziol. Nauk;,vol. 13; No. 2; pp. 93-122; 1982.
Krarup et al; Conduction studies in peripheral cat nerve using implanted electrodes: I. methods and findings in controls; Muscle & Nerve; vol. 11; pp. 922-932; Sep. 1988.
Kuznik, "Role of the vascular wall in the process of hemostatis," Usp Sovrem Biol., vol. 75(1): pp. 61-85, 1973.
Kuznik, et al., "Role of the heart and vessels in regulating blood coagulation and fibrinolysis," Kagdiologiia, vol. 13(4): pp. 145-154, 1973.
Loeb et al.; Cuff electrodes for chronic stimulation and recording of peripheral nerve activity; Journal of Neuroscience Methods; vol. 64; pp. 95-103; 1996.
Pateyuk, et al.,"Treatment of Botkin's disease with heparin," Klin. Med., vol. 51(3): pp. 113-117, 1973.
Payne, J. B. et al., Nicotine effects on PGE2 and IL-1 beta release by LPS-treated human monocytes, J. Perio. Res., vol. 31, No. 2, pp. 99-104, 1996.
Pullan, R. D., et al., Transdermal nicotine for active ulceratiive colitis, N. Engl. J. Med., vol. 330, No. 12, pp. 811-815, 1994.
Pulvirenti et al; Drug dependence as a disorder of neural plasticity:focus on dopamine and glutamate; Rev Neurosci.; vol. 12; No. 2; pp. 141-158; 2001.
Sokratov, et al. "The role of choline and adrenegic structures in regulation of renal excretion of hemocoagulating compounds into the urine," Sechenov Physiological Journal of the USSR, vol. 63(12): pp. 1728-1732, 1977.
Strojnik et al.; Treatment of drop foot using and implantable peroneal underknee stimulator; Scand. J. Rehab. Med.; vol. 19; pp. 37R43; 1987.
Takeuchi et al., A comparison between chinese blended medicine "Shoseiryuto" tranilast and ketotifen on the anit-allergic action in the guinea pigs, Allergy, vol. 34, No. 6, pp. 387-393, 1985 (eng. abstract).
Faltys et al.; U.S. Appl. No. 12/978,250 entitled "Neural stimulation devices and systems for treatment of chronic inflammation," filed Dec. 23, 2010.
Levine et al. U.S. Appl. No. 13/851,013 entitled "Devices and methods for modulation of bone erosion," filed Mar. 26, 2013.
Nadol et al., "Surgery of the Ear and Temporal Bone," Lippinkott Williams & Wilkins, 2nd Ed., 2005, (Publication date: Sep. 21, 2004), p. 580.
Levine, Jacob A.; U.S. Appl. No. 13/338,185 entitled "Modulation of sirtuins by vagus nerve stimulation" filed Dec. 27, 2011.
Robinson et al.; Studies with the Electrocardiograph on the Action of the Vagus Nerve on the Human Heart; J Exp Med; 14(3):217-234; Sep. 1911.

\* cited by examiner

NEURAL TOURNIQUET

RELATED APPLICATION

This application claims the benefit of U.S. Provisional Application No. 60/556,096, filed Mar. 25, 2004.

The entire teachings of the above application are incorporated herein by reference.

GOVERNMENT SUPPORT

The invention was supported, in whole or in part, by a grant N66001-03-1-8907 P00003 from Space and Naval Warfare Systems Center-San Diego and Defense Advanced Research Programs Agency. The Government has certain rights in the invention.

BACKGROUND OF THE INVENTION

Excessive bleeding can occur as a consequence of injury, surgery, inherited bleeding disorders, or bleeding disorders which are developed during certain illnesses (such as vitamin K deficiency, severe liver damage) or treatments (such as the use of anticoagulant drugs or prolonged use of antibiotics).

Some of the risks associated with bleeding disorders include scarring of the joints or joint disease, vision loss from bleeding into the eye, chronic anemia from blood loss, and death which may occur with large amounts of blood loss or bleeding in critical areas such as the brain.

Bleeding disorders result from an inability of the blood to clot. This inability is most commonly caused by a deficiency of blood coagulation factors. Other less common causes include a deficiency in blood platelets or a disorder in platelet function.

Hemophilia A is one of the most frequently occurring inherited coagulation disorders. Patients with hemophilia A are prone to frequent hemorrhages as a result of a deficiency in Factor VIII. Common treatments for people with bleeding disorders such as hemophilia A, include factor replacement therapy. This is the injection into the bloodstream of Factor VIII concentrates to prevent or control bleeding.

Factor replacement therapy can also be used to reduce postoperative bleeding in high risk surgical procedures. The main disadvantage of factor replacement therapy, however, is the increased risk of exposure to blood-borne infections such as hepatitis due to infusions of blood products.

SUMMARY OF THE INVENTION

It has now been discovered that bleed time can be reduced in a subject by activation of the cholinergic anti-inflammatory pathway in said subject. The cholinergic anti-inflammatory pathway can be activated by direct stimulation of the vagus nerve in the subject. For example, it has been shown by the inventor that electrical stimulation of the vagus nerve leads to decreased bleed time in laboratory mice (see Examples 1 and 2). The cholinergic anti-inflammatory pathway can also be activated by administering an effective amount of a cholinergic agonist to the subject. For example, it has been further shown by the inventor that administration of nicotine to laboratory mice, decreases bleed time in the mice (see Example 3). Based on these discoveries methods of reducing bleed time in a subject in need of such treatment are disclosed herein.

One embodiment of the present invention is a method of reducing bleed time in a subject by activating the cholinergic anti-inflammatory pathway. For example, the cholinergic anti-inflammatory pathway can be activated by stimulating the vagus nerve in the subject. The vagus nerve can be indirectly stimulated by administering an effective amount of muscarinic agonist to the subject. Suitable examples of muscarinic agonists include: muscarine, McN-A-343, MT-3 and CNI-1493. The cholinergic anti-inflammatory pathway can also be activated by administering an effective amount of cholinergic agonist to the subject. One example of a suitable cholinergic agonist is nicotine. Most preferably, the cholinergic agonist is selective for an $\alpha$-7 nicotinic receptor; examples of suitable $\alpha$-7 selective nicotinic agonists include: GTS-21, 3-(4-hydroxy-2-methoxybenzylidene) anabaseine, choline, cocaine methiodide, trans-3-cinnamylidene anabaseine, trans-3-(2-methoxy-cinnamylidene)anabaseine, or trans-3-(4-methoxycinnamylidene)anabaseine. The cholinergic anti-inflammatory pathway can also be activated by electrical stimulation of the vagus nerve in the subject or mechanical stimulation of the vagus nerve.

DETAILED DESCRIPTION OF THE INVENTION

Figure 1:
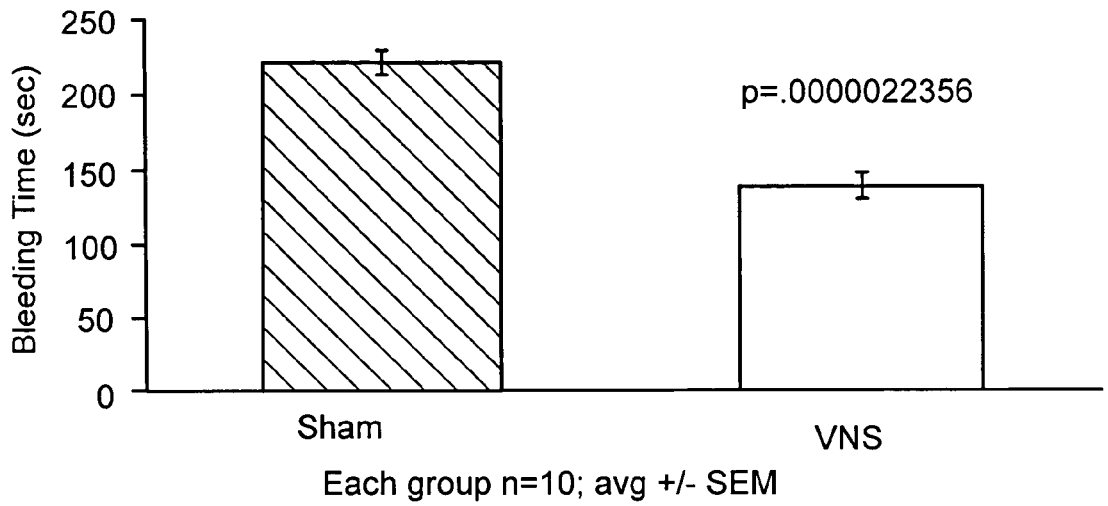
FIG. 1 is a graph showing the decrease in bleed time in seconds in laboratory mice, after vagus nerve stimulation at 1 volt for 20 minutes. This result is compared to a longer bleed time in a control group in which the vagus nerve was isolated but not stimulated.

The present invention is based on the discovery that bleed time can be reduced in a subject by activation of the cholinergic anti-inflammatory pathway (CAP) in said subject. As used herein, a subject is preferably a mammal, more preferably a human patient but can also be a companion animal (e.g., dog or cat), a farm animal (e.g., horse, cow, or sheep) or a laboratory animal (e.g., rat, mouse, or guinea pig).

The cholinergic anti-inflammatory pathway, as used herein, refers to a biochemical pathway in a subject, that is activated by cholinergic agonists and reduces inflammation in the subject. The cholinergic anti-inflammatory pathway is described in U.S. Patent Publication No. 2004/0204355 filed Dec. 5, 2003 and U.S. Pat. No. 6,610,713 filed May 15, 2001, the entire teachings of each of which are incorporated herein by reference. It has now been found that activation of the cholinergic anti-inflammatory pathway also results in the reduction of bleed time in a subject.

The cholinergic anti-inflammatory pathway may also be activated by stimulation (direct or indirect) of the vagus nerve in a subject. It is well known in the art that stimulation of the vagus nerve results in the release acetylcholine from efferent vagus nerve fibers (this is described in U.S. Pat. No. 6,610,713 B2, filed May 15, 2001, the entire teachings of which are incorporated herein by reference). As used herein, the vagus nerve includes nerves that branch off from the main vagus nerve, as well as ganglions or postganglionic neurons that are connected to the vagus nerve. The effect of vagus nerve stimulation on bleed time is not necessarily limited to that caused by acetylcholine release. The scope of the invention also encompasses other mechanisms which are partly or wholly responsible for the reduction of bleed time by vagus nerve stimulation. Nonlimiting examples include the release of serotonin agonists or stimulation of other neurotransmitters.

The terms 'reduce' or 'reduced' when referring to bleed time in a subject, encompass at least a small but measurable reduction in bleed time over non-treated controls. In preferred embodiments, the bleed time is reduced by at least 20% over non-treated controls; in more preferred embodiments, the reduction is at least 70%; and in still more preferred embodiments, the reduction is at least 80%.

In one embodiment of the present invention, activation of the cholinergic anti-inflammatory pathway, and the reduction of bleed time in a subject is achieved by indirect stimulation of the vagus nerve. As used herein, indirect stimulation includes methods which involve secondary processes or agents which stimulate the vagus nerve. One example of such a secondary agent is a pharmacological vagus nerve stimulator.

In a preferred embodiment the pharmacological vagus nerve stimulator is an agonist (such as a muscarinic agonist) that activates a muscarinic receptor in the brain. As used herein, a muscarinic agonist is a compound that can bind to and activate a muscarinic receptor to produce a desired physiological effect, here, the reduction of bleed time. A muscarinic receptor is a cholinergic receptor which contains a recognition site for a muscarinic agonist (such as muscarine). In one embodiment, the muscarinic agonist is non-selective and can bind to other receptors in addition to muscarinic receptors, for example, another cholinergic receptor. An example of such a muscarinic agonist is acetylcholine. In a preferred embodiment, the muscarinic agonist binds muscarinic receptors with greater affinity than other cholinergic receptors, for example, nicotinic receptors (for example with at least 10% greater affinity, 20% greater affinity, 50% greater affinity, 75% greater affinity, 90% greater affinity, or 95% greater affinity).

In a preferred embodiment the muscarinic agonist is selective for an M1, M2, or M4 muscarinic receptor (as disclosed in U.S. Pat. No. 6,602,891, U.S. Pat. No. 6,528,529, U.S. Pat. No. 5,726,179, U.S. Pat. No. 5,718,912, U.S. Pat. No. 5,618,818, U.S. Pat. No. 5,403,845, U.S. Pat. No. 5,175,166, U.S. Pat. No. 5,106,853, U.S. Pat. No. 5,073,560 and U.S. Patent Publication No. 2004/0048795 filed Feb. 26, 2003, the contents of each of which are incorporated herein by reference in their entirety). As used herein, an agonist that is selective for an M1, M2, or M4 receptor is an agonist that binds to an M1, M2, and/or M4 receptor with greater affinity than it binds to at least one, or at least two, or at least five other muscarinic receptor subtypes (for example, M3 or M5 muscarinic receptors) and/or at least one, or at least two, or at least five other cholinergic receptors. In a preferred embodiment, the agonist binds with at least 10% greater affinity, 20% greater affinity, 50% greater affinity, 75% greater affinity, 90% greater affinity, or 95% greater affinity than it binds to muscarinic and/or cholinergic receptor subtypes other than M1, M2, and/or M4 receptors. Binding affinities can be determined using receptor binding assays known to one of skill in the art.

Nonlimiting examples of preferred muscarinic agonists useful for these methods include: muscarine, McN-A-343, and MT-3. In a most preferred embodiment, the muscarinic agonist is N,N'-bis(3,5-diacetylphenyl)decanediamide tetrakis(amidinohydrazone)tetrahydrochloride (CNI-1493), which has the following structural formula:

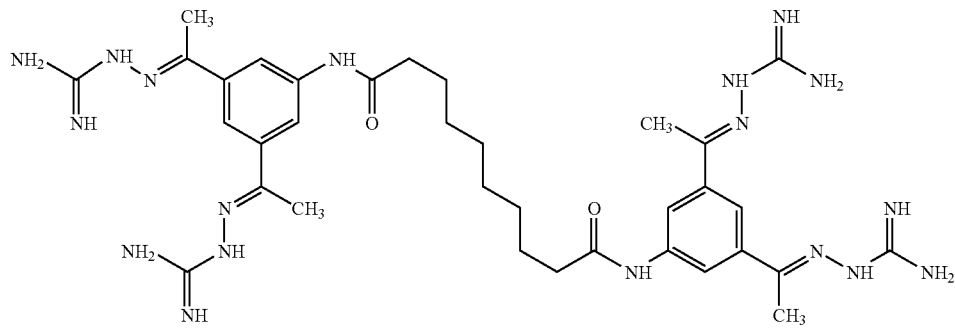 [SMILES: C/C(=N\NC(=N)N)c1cc(NC(=O)CCCCCCCCC(=O)Nc2cc(/C(C)=N/NC(=N)N)cc(/C(C)=N/NC(=N)N)c2)cc(/C(C)=N/NC(=N)N)c1]

In another embodiment, the muscarinic agonist is a CNI-1493 compound. As used herein, a CNI-1493 compound is an aromatic guanylhydrazone (more properly termed amidinohydrazone, i.e., NH$_2$(CNH)—NH—N═), for example, a compound having the structural formula I:

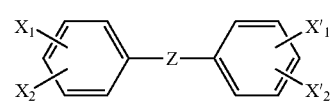

I $X_2$ is NH$_2$(CNH)—NH—N═CH—, NH$_2$(CNH)—NH—N═CCH$_3$—, or H—; $X_1$, $X'_1$ and $X'_2$ independently are NH$_2$ (CNH)—NH—N=CH— or NH$_2$(CNH)—NH—N=CCH$_3$—; Z is —NH(CO)NH—, —(C$_6$H$_4$)—, —(C$_5$H$_3$)—, or -A-(CH$_2$)$_n$-A-, n is 2-10, which is unsubstituted, mono- or di-C-methyl substituted, or a mono or di-unsaturated derivative thereof; and A, independently, is —NH(CO)—, —NH(CO)NH—, —NH—, or —O—, and pharmaceutically acceptable salts thereof. A preferred embodiment includes those compounds where A is a single functionality. Also included are compounds having the structural formula I when $X_1$ and $X_2$ are H; $X'_1$ and $X'_2$ independently are NH$_2$(CNH)—NH—N=CH— or NH$_2$(CNH)—NH—N=CCH$_3$—; Z is -A-(CH$_2$)$_n$-A-, n is 3-8; A is —NH(CO)— or —NH(CO)NH—; and pharmaceutically acceptable salts thereof. Also included are compounds of structural formula I when $X_1$ and $X_2$ are H; $X'_1$ and $X'_2$ independently are NH$_2$(CNH)—NH—N=CH— or NH$_2$(CNH)—NH—N=CCH$_3$—; Z is —O—(CH$_2$)$_2$—O—; and pharmaceutically acceptable salts thereof.

Further examples of CNI-1493 compounds include compounds of structural formula I when $X_2$ is NH$_2$(CNH)—NH—N=CH—, NH$_2$(CNH)—NH—N=CCH$_3$— or H—; $X_1$, $X'_1$ and $X'_2$ are NH$_2$(CNH)—NH—N=CH— or NH$_2$(CNH)—NH—N=CCH$_3$—; and Z is —O—(CH$_2$)$_n$—O—, n is 2-10; pharmaceutically acceptable salts thereof; and the related genus, when $X_2$ is other than H, $X_2$ is meta or para to $X_1$ and when, $X'_2$ is meta or para to $X'_1$. Another embodiment includes a compound having structural formula I when $X_2$ is NH$_2$(CNH)—NH—N=CH—, NH$_2$(CNH)—NH—N=CCH$_3$—, or H; $X_1$, $X'_1$ and $X'_2$, are NH$_2$(CNH)—NH—N=CH— or NH$_2$(CNH)—NH—N=CCH$_3$—; Z is —NH—(C=O)—NH—; pharmaceutically acceptable salts thereof; and the related genus when $X_2$ is other than H, $X_2$ is meta or para to $X_1$ and when $X'_2$ is meta or para to $X'_1$.

A CNI-1493 compound also includes an aromatic guanylhydrazone compound having the structural formula II:

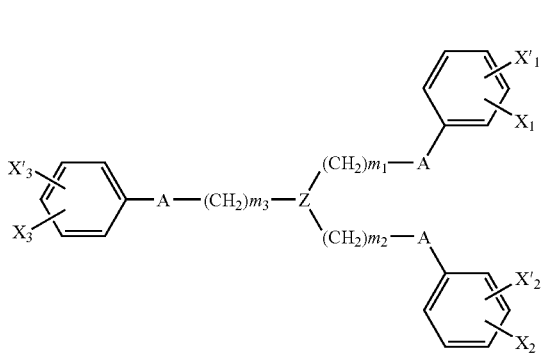

$X_1$, $X_2$, and $X_3$ independently are NH$_2$(CNH)—NH—N=CH— or NH$_2$(CNH)—NH—N=CCH$_3$—, $X'_1$, $X'_2$, and $X'_3$ independently are H, NH$_2$(CNH)—NH—N=CH— or NH$_2$(CNH)—NH—N=CCH$_3$—; Z is (C$_6$H$_3$), when m$_1$, m$_2$, and m$_3$ are 0 or Z is N, when, independently, m$_1$, m$_2$, and m$_3$ are 2-6, and A is —NH(CO)—, —NH(CO)NH—, —NH—, or —O—; and pharmaceutically acceptable salts thereof. Further examples of compounds of structural formula II include the genus wherein, when any of $X'_1$, $X'_2$, and $X'_3$ are other than H, then the corresponding substituent of the group consisting of $X_1$, $X_2$, and $X_3$ is meta or para to $X'_1$, $X'_2$, and $X'_3$, respectively; the genus when m$_1$, m$_2$, and m$_3$ are 0 and A is —NH(CO)—; and the genus when m$_1$, m$_2$, and m$_3$ are 2-6, A is —NH(CO)NH—, and pharmaceutically acceptable salts thereof. Examples of CNI-1493 compounds and methods for making such compounds are described in U.S. Pat. No. 5,854,289 (the contents of which are incorporated herein by reference).

Alternatively, the cholinergic anti-inflammatory pathway is activated by administering an effective amount of cholinergic agonist to a subject, thus reducing bleed time in said subject. As used herein, a cholinergic agonist is a compound that binds to and activates a cholinergic receptor producing a desired physiological effect, here, the reduction of bleed time in a subject. The skilled artisan can determine whether any particular compound is a cholinergic agonist by any of several well known methods. In preferred embodiments the cholinergic agonist has been used therapeutically in vivo or is naturally produced. Nonlimiting examples of cholinergic agonists suitable for use in the disclosed invention include: acetylcholine, nicotine, muscarine, carbachol, galantamine, arecoline, cevimeline, and levamisole. In a preferred embodiment the cholinergic agonist is acetylcholine, nicotine, or muscarine.

In a more preferred embodiment the cholinergic agonist is an α7 selective nicotinic cholinergic agonist. As used herein an α7 selective nicotinic cholinergic agonist is a compound that selectively binds to and activates an α7 nicotinic cholinergic receptor in a subject. Nicotinic cholinergic receptors are a family of ligand-gated, pentameric ion channels. In humans, 16 different subunits (α1-7, α9-10, β1-4, δ, ε, and γ) have been identified that form a large number of homo- and heteropentameric receptors with distinct structural and pharmacological properties (Lindstrom, J. M., Nicotinic Acetylcholine Receptors. In "Hand Book of Receptors and Channels: Ligand- and Voltage-Gated Ion Channels" Edited by R. Alan North CRC Press Inc., (1995); Leonard, S., & Bertrand, D., Neuronal nicotinic receptors: from structure to function. *Nicotine & Tobacco Res.* 3:203-223 (2001); Le Novere, N., & Changeux, J-P., Molecular evolution of the nicotinic acetylcholine receptor: an example of multigene family in excitable cells, *J. Mol. Evol.,* 40:155-172 (1995)).

As used herein, a cholinergic agonist is selective for an α7 nicotinic cholinergic receptor if that agonist activates an α7 nicotinic cholinergic receptor to a greater extent than the agonist activates at least one other nicotinic receptor. It is preferred that the α7 selective nicotinic agonist activates the α7 nicotinic receptor at least two-fold, at least five-fold, at least ten-fold, and most preferably at least fifty-fold more than at least one other nicotinic receptor (and preferably at least two, three, or five other nicotinic receptors). Most preferably, the α7 selective nicotinic agonist will not activate another nicotinic receptor to any measurable degree (i.e., significant at P=0.05 vs. untreated receptor in a well-controlled comparison).

Such an activation difference can be measured by comparing activation of the various receptors by any known method, for example using an in vitro receptor binding assay, such as those produced by NovaScreen Biosciences Corporation (Hanover Md.), or by the methods disclosed in WO 02/44176 (α4β2 tested), U.S. Pat. No. 6,407,095 (peripheral nicotinic receptor of the ganglion type), U.S. Patent Application Publication No. 2002/0086871 (binding of labeled ligand to membranes prepared from GH$_4$Cl cells transfected with the receptor of interest), and WO 97/30998. References which describe methods of determining agonists that are selective for α7 receptors include: U.S. Pat. No. 5,977,144 (Table 1), WO 02/057275 (pg 41-42), and Holladay et al., Neuronal Nicotinic Acetylcholine Receptors as Targets for Drug Discovery, Journal of Medicinal Chemistry, 40:4169-4194 (1997), the teachings of these references are incorporated herein by reference in their entirety. Assays for other nicotinic receptor subtypes are known to the skilled artisan.

In one embodiment the α7 selective nicotinic agonist is a compound of structural formula III:

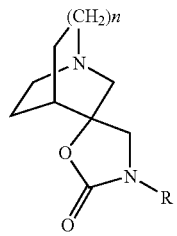

R is hydrogen or methyl, and n is 0 or 1, and pharmaceutically acceptable salts thereof. In a preferred embodiment the α7 selective nicotinic agonist is (−)-spiro[1'-azabicyclo[2.2.2]octane-3,5'-oxazolidin-2'-one]. Methods of preparation of compounds of structural formula III are described in U.S. Pat. No. 5,902,814, the contents of which are incorporated herein by reference in their entirety.

In another embodiment, the α7 selective nicotinic agonist is a compound of structural formula IV:

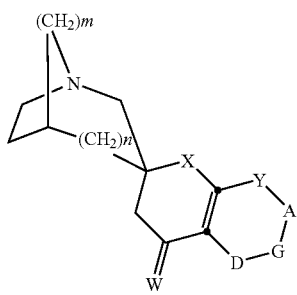

m is 1 or 2; n is 0 or 1; Y is CH, N or NO; X is oxygen or sulfur; W is oxygen, $H_2$ or $F_2$; A is N or $C(R^2)$; G is N or $C(R^3)$; D is N or $C(R^4)$; with the proviso that no more than one of A, G and D is nitrogen but at least one of G and D is nitrogen or NO; $R^1$ is hydrogen or $C_1$ to $C_4$ alkyl, $R^2$, $R^3$, and $R^4$ are independently hydrogen, halogen, $C_1$-$C_4$ alkyl, $C_2$-$C_4$ alkenyl, $C_2$-$C_4$ alkynyl, aryl, heteroaryl, OH, $OC_1$-$C_4$ alkyl, $CO_2R^1$—CN, —$NO_2$, —$NR^5R^6$, —$CF_3$, or —$OSO_2CF_3$, or $R^2$ and $R^3$, or $R^3$ and $R^4$, respectively, may together form another six membered aromatic or heteroaromatic ring sharing A and G, or G and D, respectively, containing between zero and two nitrogen atoms, and substituted with one to two of the following substitutents: independently hydrogen, halogen, $C_1$-$C_4$ alkyl, $C_2$-$C_4$ alkenyl, $C_2$-$C_4$ alkynyl, aryl, heteroaryl, OH, $OC_1$-$C_4$ alkyl, $CO_2R^1$, —CN, —$NO_2$, —$NR^5R^6$, —$CF_3$, or —$OSO_2CF_3$; $R^5$ and $R^6$ are independently hydrogen, $C_1$-$C_4$ alkyl, $C(O)R^7$, $C(O)NHR^8$, $C(O)OR^9$, $SO_2R^{10}$ or may together be $(CH_2)_jQ(CH_2)_k$, where Q is O, S, $NR^{11}$, or a bond; j is 2 to 7; k is 0 to 2; and $R^7$, $R^8$, $R^9$, $R^{10}$ and $R^{11}$ are independently $C_1$-$C_4$, alkyl, aryl, or heteroaryl; an enantiomer thereof, or a pharmaceutically acceptable salt thereof. In preferred embodiments, the α7 selective nicotinic agonist is a compound of structural formula IV when m is 2; n is 0; X is oxygen; A is $C(R^2)$; G is $C(R^3)$; and D is $C(R^4)$. In a particular preferred embodiment the α7 selective nicotinic agonist is (R)-(−)-5'-phenylspiro[1-aziobicyclo[2.2.2]octane-3,2'(3'H)-furo[2,3-b]pyridine]. Methods of preparation of compounds of structural formula IV are described in the U.S. Pat. No. 6,110,914, the contents of which are incorporated herein by reference in their entirety.

In yet another embodiment the α7 selective nicotinic agonist is a compound of structural formula V:

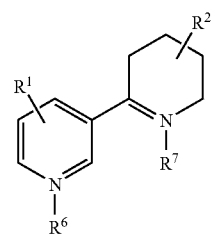

$R^1$, $R^6$ and $R^7$ are hydrogen or $C_1$-$C_4$ alkyl; alternatively $R^1$ is hydrogen or $C_1$-$C_4$ alkyl, and $R^6$ and $R^7$ are absent, hydrogen or $C_1$-$C_4$ alkyl; and $R^2$ is:

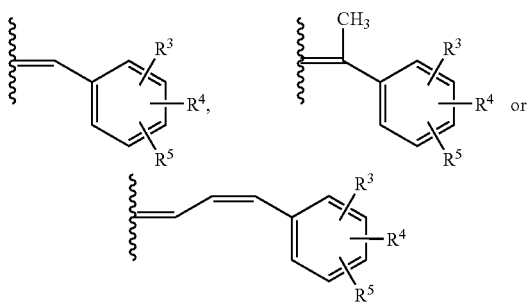

$R^3$, $R^4$, and $R^5$ are hydrogen, $C_1$-$C_4$ alkyl optionally substituted with N,N-dialkylamino having 1 to 4 carbons in each of the alkyls, $C_1$-$C_6$ alkoxy optionally substituted with N,N-dialkylamino having 1 to 4 carbons in each of the alkyls, carboalkoxy having 1 to 4 carbons in the alkoxy, amino, amido having 1 to 4 carbons in the acyl, cyano, and N,N-dialkylamino having 1 to 4 carbons in each of the alkyls, halo, hydroxyl or nitro.

In preferred embodiments, the α7 selective nicotinic agonist is a compound of structural formula V when $R^2$ is attached to the 3-position of the tetrahydropyridine ring. In another preferred embodiment when $R^3$, which may preferably be attached to the 4- or the 2-position of the phenyl ring, is: amino, hydroxyl, chloro, cyano, dimethylamino, methyl, methoxy, acetylamino, acetoxy, or nitro. In one particular preferred embodiment the α7 selective nicotinic agonist is a compound of structural formula V, when $R^3$ is hydroxyl, and $R^1$, $R^4$, and $R^5$ are hydrogen. In another particular preferred embodiment the α7 selective nicotinic agonist is a compound of structural formula V, when $R^3$ is acetylamino and $R^1$, $R^4$, and $R^5$ are hydrogen. In another particular preferred embodiment the α7 selective nicotinic agonist is a compound of structural formula V, when $R^3$ is acetoxy and $R^1$, $R^4$, and $R^5$ are hydrogen. In another particular preferred embodiment the α7 selective nicotinic agonist is a compound of structural formula V, when $R^3$ is methoxy and $R^1$, $R^4$, and $R^5$ are hydrogen. In another particular preferred embodiment the α7 selective nicotinic agonist is a compound of structural formula V, when $R^3$ is methoxy and $R^1$ and $R^4$ are hydrogen, and further when, $R^3$ is attached to the 2-position of the phenyl ring, and $R^5$, which is attached to the 4-position of the phenyl ring, is methoxy or hydroxy.

In a preferred embodiment the α7 selective nicotinic agonist is: 3-(2,4-dimethoxybenzylidine) anabaseine (GTS-21) (also known as DMXB-A), 3-(4-hydroxybenzylidene)anabaseine, 3-(4-methoxybenzylidene)anabaseine, 3-(4-aminobenzylidene)anabaseine, 3-(4-hydroxy-2-methoxybenzylidene)anabaseine, 3-(4-methoxy-2-hydroxybenzylidene) anabaseine, trans-3-cinnamylidene anabaseine, trans-3-(2-methoxy-cinnamylidene)anabaseine, or trans-3-(4-methoxycinnamylidene)anabaseine.

Methods of preparation of compounds of structural formula V are described in U.S. Pat. No. 5,977,144, and U.S. Pat. No. 5,741,802 the contents of each of which are incorporated herein by reference in their entirety.

In further embodiments the α7 selective nicotinic agonist is a compound of structural formula VI:

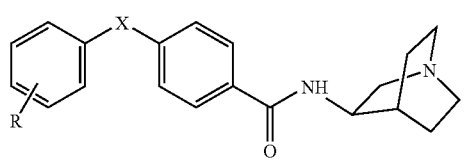

VI

X is O or S; R is H, $OR^1$, $NHC(O)R^1$, or a halogen; and $R^1$ is $C_1$-$C_4$ alkyl; or a pharmaceutically acceptable salt thereof. In a particular preferred embodiment the α7 selective nicotinic agonist is:

N-[(3R)-1-azabicyclo[2.2.2]oct-3-yl]-4-(4-hydroxyphenoxy)benzamide,
N-[(3R)-1-azabicyclo[2.2.2]oct-3-yl]-4-(4-acetamidophenoxy)benzamide,
N-[(3R)-1-azabicyclo[2.2.2]oct-3-yl]-4-(phenylsulfanyl) benzamide, or
N-[(3R)-1-azabicyclo[2.2.2]oct-3-yl]-4-(3-chlorophenylsulphonyl)benzamide.

Methods of preparation of compounds with structural formula VI have been described in the U.S. Patent Application 2002/0040035, the contents of which are incorporated herein by reference in their entirety.

In yet another embodiment the α7 selective nicotinic agonist is (1-aza-bicyclo[2.2.2]oct-3-yl)-carbamic acid 1-(2-fluorophenyl)-ethyl ester. Methods of preparation of this compound have been described in the U.S. Patent Application Publication 2002/0040035, the contents of which are incorporated herein by reference in their entirety.

In an even more preferred embodiment the α7 selective nicotinic agonist is: GTS-21, 3-(4-hydroxy-2-methoxybenzylidene)anabaseine, (R)-(−)-5'-phenylspiro[1-azabicyclo [2.2.2]octane-3,2'octane-3,2'(3'H)-furo[2,3-b]pyridine], (−)-spiro-[1-azabicyclo[2.2.2]octane-3,5'-oxazolidin-2'-one] or cocaine methiodide, additional α7 selective nicotinic agonist include trans-3-cinnamylidene anabaseine, trans-3-(2-methoxy-cinnamylidene)anabaseine or trans-3-(4-methoxycinnamylidene anabaseine.

In yet another embodiment, the α7 selective nicotinic agonist is an antibody which is a selective agonist (most preferably a specific agonist) for the α7 nicotinic receptor. The antibodies can be polyclonal or monoclonal; may be from human, non-human eukaryotic, cellular, fungal or bacterial sources; may be encoded by genomic or vector-borne coding sequences; and may be elicited against native or recombinant α7 or fragments thereof with or without the use of adjuvants, all according to a variety of methods and procedures well-known in the art for generating and producing antibodies. Other examples of such useful antibodies include but are not limited to chimeric, single-chain, and various human or humanized types of antibodies, as well as various fragments thereof such as Fab fragments and fragments produced from specialized expression systems.

In additional embodiments, the α7 selective nicotinic agonist is an aptamer which is a selective agonist (more preferably a specific agonist) for the α7 nicotinic receptor. Aptamers are single stranded oligonucleotides or oligonucleotide analogs that bind to a particular target molecule, such as a protein or a small molecule (e.g., a steroid or a drug, etc.). Thus aptamers are the oligonucleotide analogy to antibodies. However, aptamers are smaller than antibodies, generally in the range of 50-100 nt. Their binding is highly dependent on the secondary structure formed by the aptamer oligonucleotide. Both RNA and single stranded DNA (or analog), aptamers are known. See, e.g., Burke et al., *J. Mol. Biol.*, 264(4): 650-666 (1996); Ellington and Szostak, *Nature*, 346 (6287): 818-822 (1990); Hirao et al., *Mol Divers.*, 4(2): 75-89 (1998); Jaeger et al., *The EMBO Journal* 17(15): 4535-4542 (1998); Kensch et al., *J. Biol. Chem.*, 275(24): 18271-18278 (2000); Schneider et al., *Biochemistry*, 34(29): 9599-9610 (1995); and U.S. Pat. Nos. 5,496,938; 5,503,978; 5,580,737; 5,654,151; 5,726,017; 5,773,598; 5,786,462; 6,028,186; 6,110,900; 6,124,449; 6,127,119; 6,140,490; 6,147,204; 6,168,778; and 6,171,795. Aptamers can also be expressed from a transfected vector (Joshi et al., *J. Virol.*, 76(13), 6545-6557 (2002)).

Aptamers that bind to virtually any particular target can be selected by using an iterative process called SELEX, which stands for Systematic Evolution of Ligands by EXponential enrichment (Burke et al., *J. Mol. Biol.*, 264(4): 650-666 (1996); Ellington and Szostak, *Nature*, 346(6287): 818-822 (1990); Schneider et al., *Biochemistry*, 34(29): 9599-9610 (1995); Tuerk et al., *Proc. Natl. Acad. Sci. USA*, 89: 6988-6992 (1992); Tuerk and Gold, *Science*, 249(4968): 505-510 (1990)). Several variations of SELEX have been developed which improve the process and allow its use under particular circumstances. See, e.g., U.S. Pat. Nos. 5,472,841; 5,503, 978; 5,567,588; 5,582,981; 5,637,459; 5,683,867; 5,705,337; 5,712,375; and 6,083,696. Thus, the production of aptamers to any particular oligopeptide, including the α7 nicotinic receptor, requires no undue experimentation.

As described above, the compounds can be administered in the form of a pharmaceutically acceptable salt. This includes compounds disclosed herein which possess a sufficiently acidic, a sufficiently basic, or both functional groups, and accordingly can react with any of a number of organic or inorganic bases, and organic or inorganic acids, to form a salt. Acids commonly employed to form acid addition salts from compounds with basic groups, are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, -benzyl-β-phenethylamine, dehydroabietylamine, N,N'-bisdehydroabietylamine, glucamine, N-methylglucamine, collidine, quinine, quinoline, and basic amino acid such as lysine and arginine. These salts may be prepared by methods known to those skilled in the art.

The term "alkyl", as used herein, unless otherwise indicated, includes saturated monovalent hydrocarbon radicals having straight or branched moieties, typically $C_1$-$C_{10}$, preferably $C_1$-$C_6$. Examples of alkyl groups include, but are not limited to, methyl, ethyl, propyl, isopropyl, and t-butyl.

The term "alkenyl", as used herein, includes alkyl moieties, as defined above, having at least one carbon-carbon double bond. Examples of alkenyl groups include, but are not limited to, ethenyl and propenyl.

The term "alkynyl", as used herein, includes alkyl moieties, as defined above, having at least one carbon-carbon triple bond. Examples of alkynyl groups include, but are not limited to, ethynyl and 2-propynyl.

The term "alkoxy", as used herein, means an "alkyl-O-" group, wherein alkyl is defined above.

The term "cycloalkyl", as used herein, includes non-aromatic saturated cyclic alkyl moieties, wherein alkyl is as defined above. Examples of cycloalkyl include, but are not limited to, cyclopropyl, cyclobutyl, cyclopentyl, cyclohexyl, and cycloheptyl. "Bicycloalkyl" groups are non-aromatic saturated carbocyclic groups consisting of two rings. Examples of bicycloalkyl groups include, but are not limited to, bicyclo-[2.2.2]-octyl and norbornyl. The term "cycloalkenyl" and "bicycloalkenyl" refer to non-aromatic carbocyclic, cycloalkyl, and bicycloaklkyl moieties as defined above, except comprising of one or more carbon-carbon double bonds connecting carbon ring members (an "endocyclic" double bond) and/or one or more carbon-carbon double bonds connecting a carbon ring member and an adjacent non-ring carbon (an "exocyclic" double bond). Examples of cycloalkenyl groups include, but are not limited to, cyclopentenyl and cyclohexenyl. A non-limiting example of a bicycloalkenyl group is norborenyl. Cycloalkyl, cycloalkenyl, bicycloalkyl, and bicycloalkenyl groups also include groups similar to those described above for each of these respective categories, but which are substituted with one or more oxo moieties. Examples of such groups with oxo moieties include, but are not limited to, oxocyclopentyl, oxocyclobutyl, ococyclopentenyl, and norcamphoryl.

The term "cycloalkoxy", as used herein, includes "cycloalkyl-O-" group, wherein cycloalkyl is defined above.

The term "aryl", as used herein, refers to carbocyclic group. Examples of aryl groups include, but are not limited to, phenyl and naphthyl.

The term "heteroaryl", as used herein, refers to aromatic groups containing one or more heteroatoms (O, S, or N). A heteroaryl group can be monocyclic or polycyclic. The heteroaryl groups of this invention can also include ring systems substituted with one or more oxo moieties. Examples of heteroaryl groups include, but are not limited to, pyridinyl, pyridazinal, imidaxolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotirazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furophridinyl, pyrolopyrimidinyl, and azaindoyl.

The foregoing heteroaryl groups may be C-attached or N-attached (where such is possible). For instance, a group derived from pyrrole may be pyrrol-1-yl (N-attached) or pyrrol-3-yl (C-attached).

In the context of the present invention, a bicyclic carbocyclic group is a bicyclic compound holding carbon only as a ring atom. The ring structure may in particular be aromatic, saturated, or partially saturated. Examples of such compounds include, but are not limited to, indanyl, naphthalenyl or azulenyl.

In the context of the present invention, an amino group may be primary (—$NH_2$), secondary (—$NHR_a$), or tertiary (—$NR_aR_b$), wherein $R_a$ and $R_b$ may be: alkyl, alkenyl, alkynyl, alkoxy, cycloalkyl, cycloalkoxy, aryl, heteroaryl, or a bicyclic carbocyclic group.

In another embodiment, activation of the cholinergic anti-inflammatory pathway, and the reduction of bleed time in a subject is achieved by indirect stimulation of the vagus nerve. The method comprises administering to the subject an effective amount of a non-steriodal anti-inflammatory drug (NSAID). Examples of suitable NSAIDs include: aspirin, indomethacin, and ibuprofen. Alternatively, indirect stimulation of the vagus nerve is achieved by administering to the subject an effective amount of amiodarone or α-melanocyte-stimulating hormone (MSH).

The route of administration of the pharmacological vagus nerve stimulators (i.e., muscarinic agonists, NSAIDs, AMSH, and amiodarone) and the cholinergic agonists depends on the condition to be treated. The route of administration and the dosage to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual subject, and the severity of the subject's symptoms.

Compositions useful for the present invention can be administered parenterally such as, for example, by intravenous, intramuscular, intrathecal, or subcutaneous injection. Parenteral administration can be accomplished by incorporating the drug into a solution or suspension. Such solutions or suspensions may also include sterile diluents such as water for injection, saline solution, fixed oils, polyethylene glycols, glycerine, propylene glycol, or other synthetic solvents. Parenteral formulations may also include antibacterial agents such as, for example, benzyl alcohol, or methyl parabens, antioxidants, such as, for example, ascorbic acid or sodium bisulfite and chelating agents such as EDTA. Buffers such as acetates, citrates, or phosphates and agents for the adjustment of tonicity such as sodium chloride or dextrose may also be added. The parenteral preparation can be enclosed in ampules, disposable syringes, or multiple dose vials made of glass or plastic.

Rectal administration includes administering the pharmaceutical compositions into the rectum or large intestine. This can be accomplished using suppositories or enemas. Suppository formulations can be made by methods known in the art. For example, suppository formulations can be prepared by heating glycerin to about 120° C., dissolving the drug in the glycerin, mixing the heated glycerin after which purified water may be added, and pouring the hot mixture into a suppository mold.

Transdermal administration includes percutaneous absorption of the drug through the skin. Transdermal formulations include patches, ointments, creams, gels, salves, and the like. In a preferred embodiment the cholinergic agonist, nicotine, is administered transdermally by means of a nicotine patch.

A transesophageal device includes a device deposited on the surface of the esophagus which allows the drug contained within the device to diffuse into the blood which perfuses the esophageal tissue.

The present invention includes nasally administering to the subject an effective amount of the drug. As used herein, nasal administration includes administering the drug to the mucous membranes of the nasal passage or nasal cavity of the subject. As used herein, pharmaceutical compositions for nasal administration of a drug include effective amounts of the drug prepared by well-known methods to be administered, for example, as a nasal spray, nasal drop, suspension, gel, ointment, cream, or powder. Administration of the drug may also take place using a nasal tampon, or nasal sponge.

Accordingly, drug compositions designed for oral, lingual, sublingual, buccal, and intrabuccal administration can be used with the disclosed methods and made without undue experimentation by means well known in the art, for example, with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums, and the like.

Tablets, pills, capsules, troches, and the like may also contain binders, recipients, disintegrating agent, lubricants, sweetening agents, and flavoring agents. Some examples of binders include microcrystalline cellulose, gum tragacanth, or gelatin. Examples of excipients include starch or lactose. Some examples of disintegrating agents include alginic acid, corn starch, and the like. Examples of lubricants include magnesium stearate or potassium stearate. An example of a glidant is colloidal silicon dioxide. Some examples of sweetening agents include sucrose, saccharin, and the like. Examples of flavoring agents include peppermint, methyl salicylate, orange flavoring, and the like. Materials used in preparing these various compositions should be pharmaceutically pure and nontoxic in the amounts used.

Muscarinic agonists, can be administered orally, parenterally, intranasally, vaginally, rectally, lingually, sublingually, buccaly, intrabuccaly, or transdermally to the subject as described above, provided the muscarinic agonist can cross the blood-brain barrier or permeate the brain through circumventricular organs which do not have a blood brain barrier. Brain muscarinic agonists can also be administered by intracerebroventricular injection. NSAIDs, amiodarone, and αMSH may also be administered by intracerebroventricular injection or by one of the techniques described above, provided that they can permeate the brain through the blood-brain barrier or through circumventricular organs which do not have a blood brain barrier.

An effective amount, is defined herein as a therapeutically or prophylactically sufficient amount of the drug to achieve the desired biological effect, here, the reduction of bleed time in a subject. Examples of effective amounts typically range from about 0.5 g/25 g body weight to about 0.0001 ng/25 g body weight, and preferably about 5 mg/25 g body to about 1 ng/25 g body weight.

Yet another embodiment of the present invention is directed to methods of reducing bleed time in a subject. The methods comprise activating the cholinergic anti-inflammatory pathway by directly stimulating the vagus nerve. As used herein, direct stimulation of the vagus nerve includes processes which involve direct contact with the vagus nerve or an organ served by the vagus nerve. One example of such a process, is electrical stimulation of the vagus nerve. Direct stimulation of the vagus nerve releases acetylcholine which results in the reduction of bleed time in the brain or in peripheral organs served by the vagus nerve. The vagus nerve enervates principal organs including, the pharynx, the larynx, the esophagus, the heart, the lungs, the stomach, the pancreas, the spleen, the kidneys, the adrenal glands, the small and large intestine, the colon, and the liver.

The vagus nerve can be stimulated by stimulating the entire vagus nerve (i.e., both the afferent and efferent nerves), or by isolating efferent nerves and stimulating them directly. The latter method can be accomplished by separating the afferent from the efferent fibers in an area of the nerve where both types of fibers are present. Alternatively, the efferent fiber is stimulated where no afferent fibers are present, for example close to the target organ served by the efferent fibers. The efferent fibers can also be stimulated by stimulating the target organ directly, e.g., electrically, thus stimulating the efferent fibers that serve that organ. In other embodiments, the ganglion or postganglionic neurons of the vagus nerve can be stimulated. The vagus nerve can also be cut and the distal end can be stimulated, thus only stimulating efferent vagus nerve fibers.

The vagus nerve can be directly stimulated by numerous methods. Nonlimiting examples include: mechanical means such as a needle, ultrasound, or vibration; electromagnetic radiation such as infrared, visible or ultraviolet light and electromagnetic fields; heat, or another energy source. Mechanical stimulation can also be carried out by carotid massage, oculocardiac reflex, dive reflex and valsalva maneuver. The efferent vagal nerve fibers can also be stimulated by electromagnetic radiation such as infrared, visible or ultraviolet light; heat, or any other energy source.

In preferred embodiments, the vagus nerve is directly stimulated electrically, using for example a commercial vagus nerve stimulator such as the Cyberonics NCP®, or an electric probe. The amount of stimulation useful to reduce bleed time can be determined by the skilled artisan without undue experimentation. Examples of effective amounts of electrical stimulation required to reduce bleed time include, but are not limited to, a constant voltage of 0.1, 0.5, 1, 2, 3, 5, or 10 V, at a pulse width of 2 ms and signal frequency of 1-5 Hz, for 5 seconds, 10 seconds, 30 seconds, 1 minute, 5 minutes, 10 minutes, 20 minutes, 30 minutes, or 1 hour. Alternatively, the electrical stimulation required to reduce bleed time include, but are not limited to, a constant voltage of from about 0.01 to 1 V or from about 0.01 to 0.1 V or from about 0.01 to 0.05V; a signal current range from about 1 mA to about 100 mA, from about 1 mA to about 10 mA from about 1 mA to about 5 mA; a pulse width from about 0.1 to about 5 ms; signal frequencies of about 0.1 to about 30 Hz, or from about 1 to about 30 Hz, or from about 10 to about 30 Hz; a signal on-time from about 1 to about 120 seconds, or from about 10 to about 60 seconds, or from about 20 to about 40 seconds; signal off-time from 5 minutes, up to 2 hours, over 2 hours, over 4 hours, over 8 hours, over 12 hours, or from about 2 to about 48 hours, from about 4 to about 36 hours, from about 6 to about 36 hours, from about 12 to about 36 hours, from about 16 to about 30 hours, from about 20 to about 28 hours. Alternatively, signal off-time can be undefined as one skilled in the art will readily determine the desired time interval between two consecutive signals.

Examples include, signal voltage to a range from about 0.01 V to about 1 V; pulse width to a range from about 0.1 ms to about 5 ms; signal frequency to a range from about 0.1 Hz to about 30 Hz; signal on-time from about 1 second to about 120 seconds. Signal off-time can be undefined. A signal voltage from about 0.01 V to about 0.1 V; pulse width to a range of about 0.1 ms to about 1 ms; signal frequency to a range from about 1 Hz to about 30 Hz; signal on-time to a range of from about 10 seconds to about 60 seconds; signal off-time to a range of over 2 hours. A signal voltage to a range from about 0.01 V to about 0.05 V; pulse width to a range from about 0.1 ms to about 0.5 ms; signal to a range from about 10 Hz to about 30 Hz; signal on-time to a range from about 20 seconds to about 40 seconds; signal off-time to a range from about 2 hours to about 24 hours. A signal current from about 1 mA to about 5 mA; pulse width to a range from about 0.1 ms to about 0.5 ms; signal to a range of about 10 Hz to about 30 Hz; signal on-time to a range from about 20 seconds to about 40 seconds; signal off-time can be undefined.

In certain embodiments, electrical vagal nerve stimulation which is sufficient to activate the cholinergic anti-inflammatory pathway in a subject does not decrease the heart rate of the subject.

In a preferred embodiment the vagus nerve is stimulated directly by means of an implanted device.

In another embodiment the cholinergic anti-inflammatory pathway is activated by administering an effective amount of acetylcholinesterase inhibitor to the subject. Examples of acetylcholinesterase inhibitors include: tacrine, donepezil, rivastigmine, galantamine, metrifonate, physostigmine, neostigmine, edrophonium, pyridostigmine, demacarium, and ambenonium.

In a still further embodiment the present invention is directed to reducing bleed time in a subject, the method comprising conditioning the subject to reduce bleed time by associating the activation of the cholinergic anti-inflammatory pathway with a sensory stimulus. Conditioning is a method of training an animal by which a perceptible neutral stimulus is temporarily associated with a physiological stimulus so that the animal will ultimately respond to the neutral stimulus as if it were the physiological stimulus. Pavlov, for instance, trained dogs to respond with salivation to the ringing of a bell following prior experiments where the dogs were prescribed a food stimulus (associated with salivation) simultaneously with a ringing bell stimulus.

Thus, the present invention is directed to methods of conditioning a subject to reduce bleed time in the subject upon experiencing a sensory stimulus. The methods comprise the following steps:
  (a) activating the cholinergic anti-inflammatory pathway, and providing the sensory stimulus to the subject within a time period sufficient to create an association between the stimulus and the stimulation of the vagus nerve; and
  (b) repeating step (a) at sufficient time intervals and duration to reinforce the association sufficiently for the bleed time to be reduced by the sensory stimulus alone.

In the conditioning step of these methods (step (a)), the CAP can be activated by any means previously discussed. The time interval between repetitions of the stimulus-activation procedures should also be short enough to optimize the reinforcement of the association. A common time interval is twice daily. The duration of the conditioning should also be sufficient to provide optimum reinforcement of the association. A common duration is at least one week. Optimum time intervals and durations can be determined by the skilled artisan without undue experimentation by standard methods known in the art.

The sensory stimulus can be from any of the five senses. Nonlimiting examples of suitable sensory stimuli are sounds such as a bell ring, a buzzer, and a musical passage; a touch such as a pin stick, a feather touch, and an electric shock; a taste, or the ingestion of a particular chemical, such as a sweet taste, a sour taste, a salty taste, and saccharine ingestion; and a visual image such as a still picture, a playing card, or a short video presentation.

The methods of the present invention are ideally suited to therapeutically or prophylactically treat subjects suffering from or at risk from suffering from excessive bleeding due to injury, surgery, or bleeding disorders such as: Hemophilia A, Hemophilia B, von Willebrand Disease, Afibrinogenemia, Factor II Deficiency, Parahemophilia, Factor VII Deficiency, Stuart Prower Factor Deficiency, Hageman Factor Deficiency, Fibrin Stabilizing Factor Deficiency, Thombophilia, heridetary platelet function disorders (for example: Bernard-Soulier Syndrome, Glanzmann Thrombasthenia, Gray Platelet Syndrome, Scott Syndrome, May-Hegglin Anomaly, Alport Syndrome and Wiskott-Aldrich Syndrome), or acquired platelet function disorders (such as those caused by common drugs: blood thinners, antibiotics and anaesthetics and those caused by medical conditions such as: leukemia, heart bypass surgery and chronic kidney disease). The method is particularly suitable for subjects with bleeding disorders about to undergo, or undergoing surgery.

The invention is illustrated by the following examples which are not intended to be limiting in any way.

EXEMPLIFICATION

Example 1

Reduction of Bleed Time in Mouse Model (Male BALB/c Mice) with Electrical Stimulation of the Vagus Nerve The mice were divided into two groups. In both groups the mice necks were dissected down to the musculature and the left vagus nerves were isolated. In the first group a 1 volt electric current was passed through the vagus nerve for 20 minutes. In the second group, the control group, the vagus nerve was isolated only, and the group was untreated for 20 minutes.

The mice tails from both groups were warmed in 37° C. saline for five minutes. The tails were then cut 2 mm from the tip, and the tail blood was collected in a 37° C. saline solution.

The results of the experiment are presented in FIG. 1. Electrical stimulation of the vagus nerve significantly reduced bleed time in the mice compared with the control group, thus demonstrating that stimulation of the vagus nerve decreases peripheral bleed time in a subject.

Example 2

Reduction in Bleed Time in Mouse Model (Male BALB/c Mice) with Electrical Stimulation of the Vagus Nerve The mice were divided into two groups. In both groups the mice necks were dissected down to the musculature. The mice tails from both groups were warmed in 37° C. saline for five minutes.

In both groups the left vagus nerves were isolated. In the first group a 1 volt electric current was passed through the vagus nerve for 30 seconds. The second group, the control group, was untreated for 30 seconds.

The tails were then cut 2 mm from the tip, and the tail blood was collected in a 37° C. saline solution.

Figure 2:
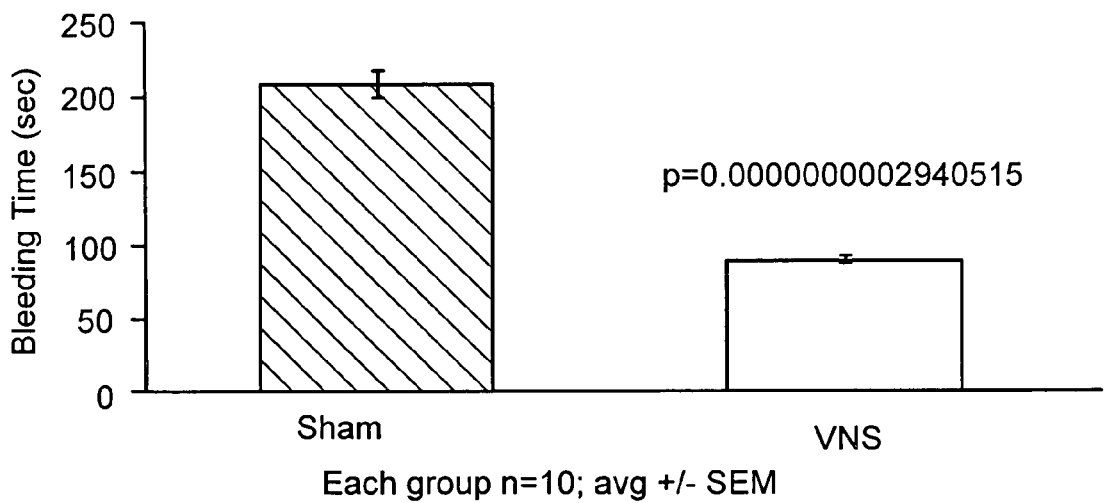
FIG. 2 is a graph showing the decrease in bleed time in seconds in laboratory mice, after vagus nerve stimulation at 1 volt for 30 seconds. This result is compared to a longer bleed time in a control group in which the vagus nerve was isolated but not stimulated.

The results of this experiment are presented in FIG. 2. Two parameters in this example were changed from Example 1, firstly the duration of stimulation was decreased from 20 minutes to 30 seconds and secondly the mice tails were pre-warmed prior to vagus nerve stimulation. The purpose of prewarming the mice tails prior to vagus nerve stimulation was to minimize the delay between stimulation and transection. This reduction in the delay between stimulation and transection resulted in a reduction in bleed time comparable with that shown in Example 1 where the mice tails were pre-warmed between the electrical stimulation and transection steps.

Example 3

Reduction of Bleed Time in Mouse Model (Male Balb/c Mice) with Administration of Nicotine The mice were weighed, and ketamine (100 mg/kg) and xylazine (10 mg/kg) was administered to each mouse.

The mice were then divided into two groups. After 20 minutes group one was injected with nicotine (0.3 mg/kg) and the second group, the control group was injected with saline. The nicotine solution was taken from a 162 mg/ml stock solution and diluted 1:10 in ethanol and then further diluted 1:250 in phosphate buffer saline (PBS), bringing the final solution to 0.0648 µg/µl; 115 µl/25 g mouse was injected into the mice.

After five minutes the two groups were injected with a saline solution.

After 20 minutes the mice tails from the two groups of mice were warmed by stirring in 37° C. water. The tails were then cut 2 mm from the tip with a fresh scalpel. The tails were immediately immersed in a fluorescent activated sorting (FACS) tube which contained 3 ml pre-warmed saline. The tubes were held in a beaker of 37° C. water which was continuously stirred. The tails remained near the bottom of the tube the entire bleeding period.

The bleeding time was counted using a stopwatch.

The mice were then euthanized by $CO_2$ via a cardiac puncture with a heparinized needle.

Figure 3:
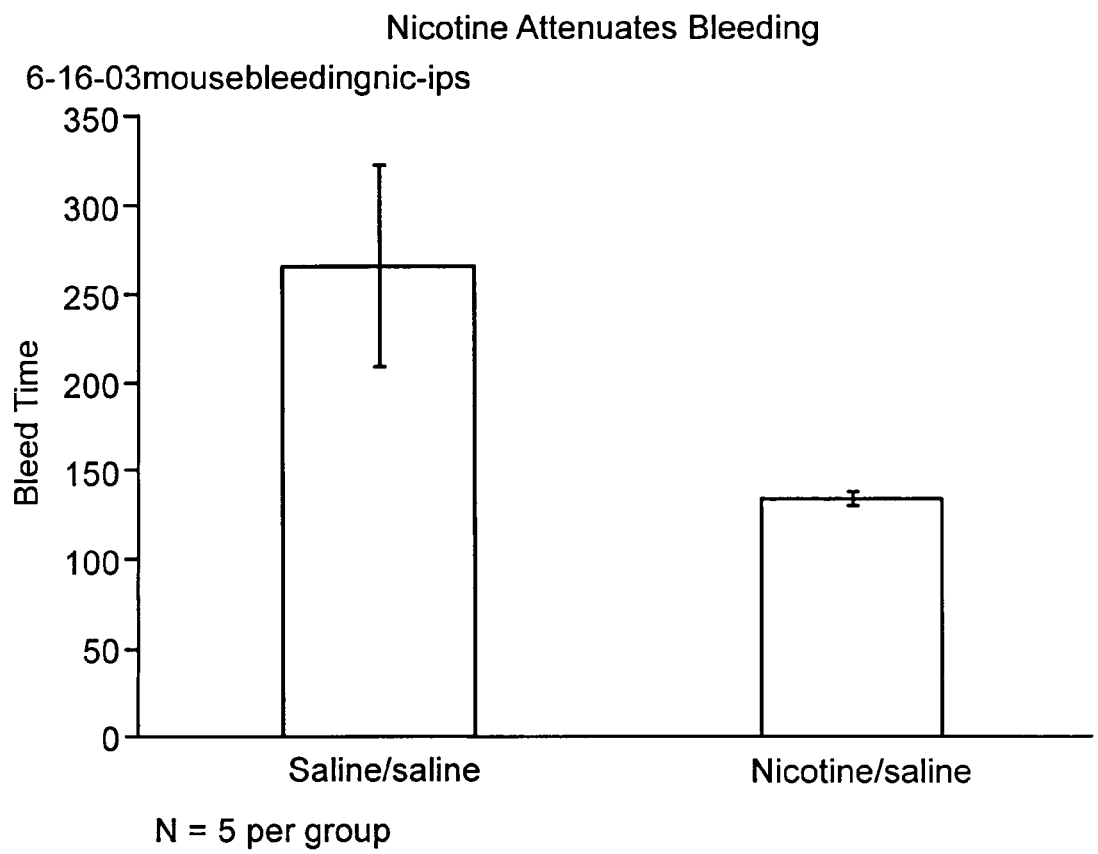
FIG. 3 is a graph showing the decrease in bleed time in seconds in laboratory mice after administration of nicotine. This result is compared to a longer bleed time in a control group to which a saline solution was administered.

Administration of nicotine to the mice significantly reduced the bleed time, thus establishing that the activation of the cholinergic anti-inflammatory pathway by cholinergic agonists reduces peripheral bleed time in the subject. The results of this experiment are presented in FIG. 3.

Example 4

Figure 4:
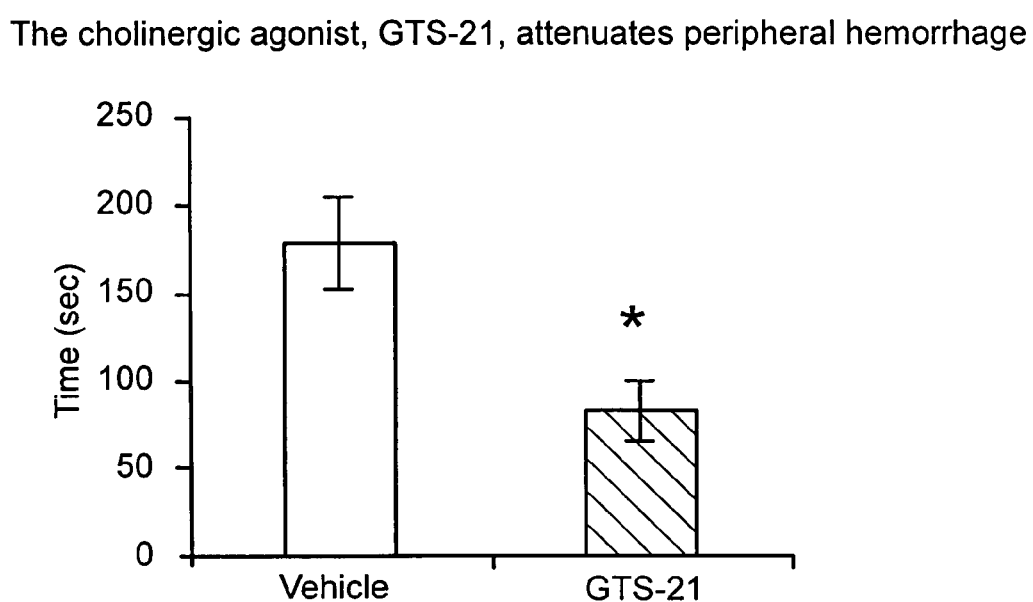
FIG. 4 is a graph showing the decrease in bleed time in seconds in two groups of laboratory mice after tail amputation. The first group was administered GTS-21 prior to amputation; a control group was administered saline.

Reduction of Bleed Time in Mouse Model (Male Balb/c Mice) by Cholinergic Agonists Male Balb/c mice (around 25 g) were injected (intraperitoneally (IP)) with cholinergic agonist GTS-21 (4 mg/kg in 125 µL PBS) or PBS (vehicle control, 125 µL). 1 hour later, mice were anesthetized with ketamine/xylazine (100 mg/kg/10 mg/kg, intraperitoneally). After immersing tails in 37° C. saline for 5 minutes to normalize vasodilatory state, 2 mm of tail was amputated with a scalpel, and returned to the saline bath (modified from Nagashima et al., *Journal of Clinical Investigation* (109) 101-110, (2002); Snyder et al., *Nature Medicine* (5), 64-70, (1999). Total bleeding time was recorded; bleeding was considered to have stopped when no signs of bleeding were observed for 30 seconds. Once bleeding stopped, animals were euthanized by $CO_2$ asphyxiation. Data were recorded in seconds, and are presented as mean+/−Standard Error (SE). Student's t-test was used for statistical analysis. The results are shown in FIG. 4.

Administration of GTS-21 to the mice significantly reduced the bleed time, thus establishing that the activation of the cholinergic anti-inflammatory pathway by cholinergic agonists reduces peripheral bleed time in the subject.

Example 5

Coagulation Cascade Measurements

Male Balb/c mice (around 25 g) were subjected to either left vagus nerve isolation only (sham surgery) or left vagus nerve electrical stimulation (1 Volt, 2 ms pulse width, 1 Hz) for 30 seconds. Immediately following stimulation, animals were euthanized, and blood was obtained by cardiac puncture and analyzed with a Hemochron JR whole blood microcoagulation system (International Technidyne Corp, Edison N.J.). Each specific test cuvette: Prothrombin Time (PT), Activated Partial Thromboplastin Time (APTT), Activated clotting time (ACT) is a self-contained disposable test chamber preloaded with a dried preparation of chemical reagents, stabilizers and buffers. The test cuvette was loaded with 50 µl of fresh whole blood. After mixing with cuvette reagents, the sample was monitored for clot formation until the clot endpoint value was achieved. Data are presented as mean+/−Standard Error of the Mean (SEM), and were analyzed by Student's t-test. The results are shown in FIGS. 5-7.

Figure 5:
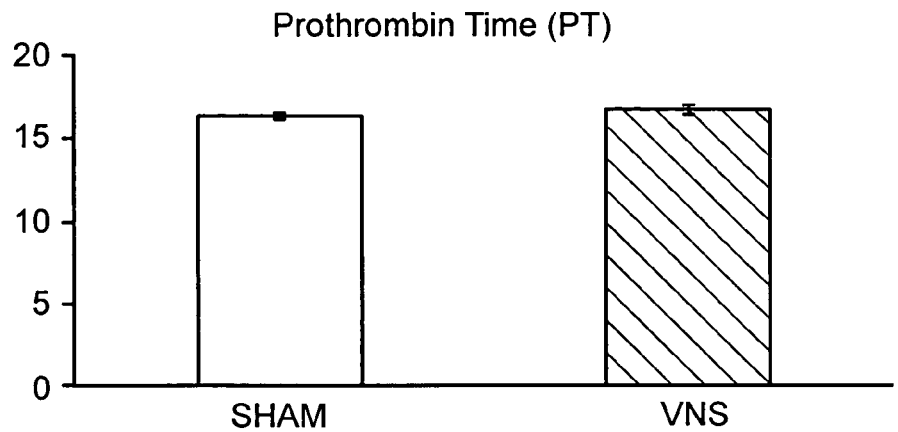
FIG. 5 is a graph showing the prothrombin time in (PT) seconds in laboratory mice after electrical vagus nerve stimulation (1V, 2 ms pulse width, 1 Hz for 30 seconds).
Figure 6:
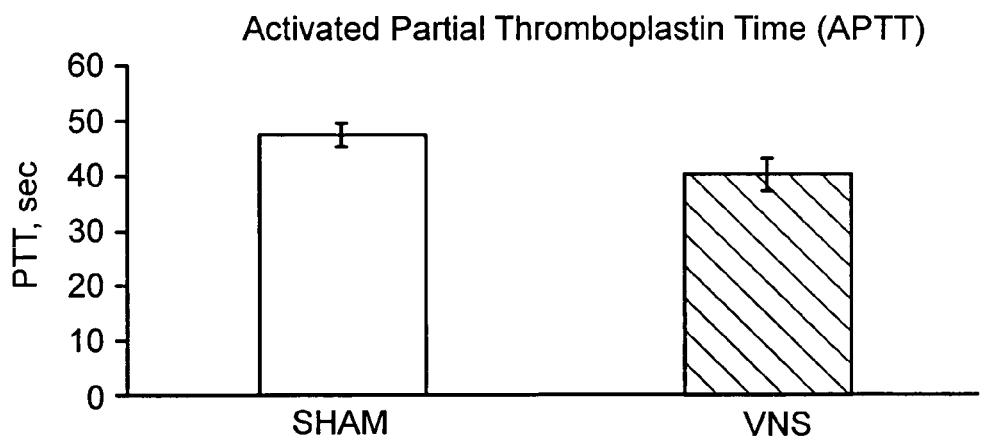
FIG. 6 is a graph showing the activated partial thromboplastin (APTT) time in seconds in laboratory mice after electrical vagus nerve stimulation (1V, 2 ms pulse width, 1 Hz for 30 seconds).
Figure 7:
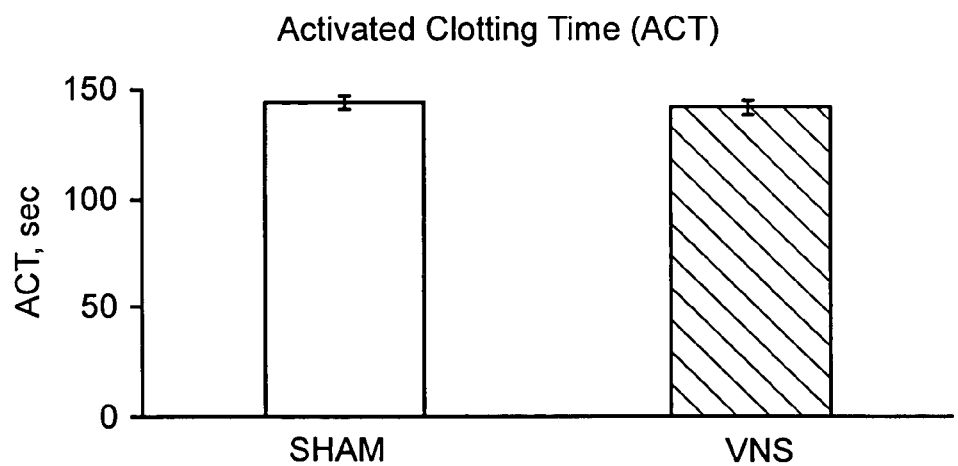
FIG. 7 is a graph showing the activated clotting time (ACT) in seconds in laboratory mice after electrical vagus nerve stimulation (1V, 2 ms pulse width, 1 Hz for 30 seconds).

FIGS. 5-7 demonstrate that the coagulation cascade is not significantly affected by vagus nerve stimulation.

Example 6

Inhibition of Bleed Time in Conscious Mice by Cholinergic Agonists

Figure 8:
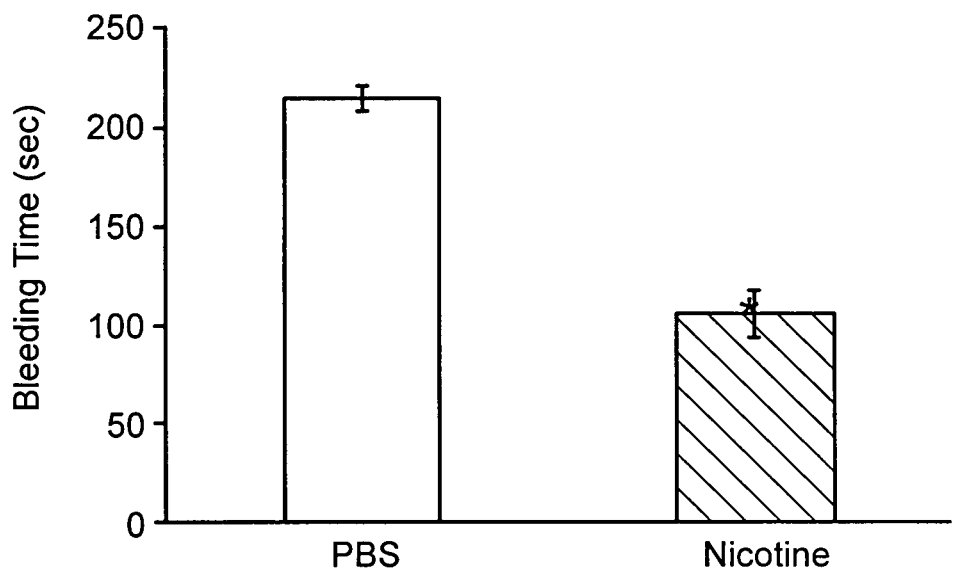
FIG. 8 is a graph showing the decrease in bleed time in seconds in conscious laboratory mice after administration of nicotine. This result is compared to a longer bleed time in a control group to which a saline solution was administered.

Animals were injected (intraperitoneally) with cholinergic agonist nicotine (0.3 mg/kg in 125 µL PBS; n=7) or PBS (vehicle control, 125 µL; n=4). 1 hour later, mice were placed in a restraint device, and the tails immersed in 37° C. water for 5 minutes. 20 mm of tail was amputated with a scalpel, and the truncated tail was placed in 37° C. saline. Total bleeding time was measured with a stop watch. Timing was stopped when no visual evidence of bleeding was noted, and no re-bleeding occurred for 30 seconds. Data were recorded in seconds, and are presented as mean+/−SE. Student's t-test was used for statistical analysis. The results can be seen in FIG. 8.

Administration of nicotine to the mice significantly reduced the bleed time, thus establishing that the activation of the cholinergic anti-inflammatory pathway by cholinergic agonists reduces peripheral bleed time in the conscious subject.

Example 7

Effect of Administration of Alpha-7 Antagonist MLA on Reduction of Bleed Time Prior to Administration of Nicotine Male Balb/c mice (around 25 g) were divided into three groups: A, B and C. Groups A and C were injected with the alpha-7 antagonist methyllycaconitine, (MLA; 4 mg/kg, IP, in 200 μL PBS), group B was injected with PBS (vehicle control, 125 μl). 15 minutes later, Group A was injected with PBS (vehicle control, 125 μl) and groups B and C were injected with nicotine (0.3 mg/kg in 125 μL PBS). 30 minutes later, mice were anesthetized (ketamine [100 mg/kg, IP] and xylazine [10 mg/kg, IP]). After immersing tails in 37° C. saline for 5 minutes to normalize vasodilatory state, 2 mm of tail was amputated with a scalpel, and returned to the saline bath (modified from Nagashima et al., *Journal of Clinical Investigation* (109) 101-110, (2002); Snyder et al., *Nature Medicine* (5), 64-70, (1999).

Total bleeding time was recorded; bleeding was considered to have stopped when no signs of bleeding were observed for 30 seconds. Once bleeding stopped, animals were euthanized by $CO_2$ asphyxiation. Data were recorded in seconds, and are presented as mean+/−SE. Student's t-test was used for statistical analysis.

Figure 9:
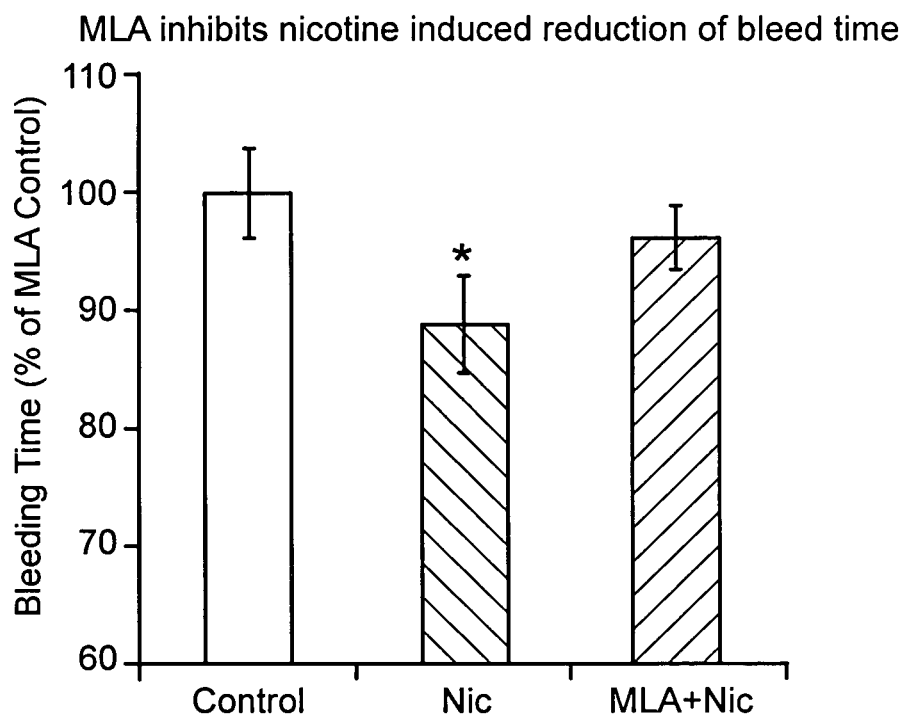
FIG. 9 is a graph showing the effect of administration of the alpha-7 antagonist MLA to mice prior to administration of nicotine.

The results are shown in FIG. 9 which shows a reduction in bleed time following administration of nicotine. MLA inhibited nicotine induced reduction of bleed time, suggesting that nicotine reduced bleed time via alpha-7 cholinergic receptor subunit.

What is claimed is:

1. A method of reducing bleed time in a subject suffering bleeding, the method comprising activating the cholinergic anti-inflammatory pathway by stimulating the vagus nerve with a signal current of less than 10 mA; and reducing bleed time of the bleeding by at least 20%.

2. The method of claim 1 wherein the subject is a human.

3. The method of claim 1 wherein the cholinergic anti-inflammatory pathway is activated by stimulating the vagus nerve in the brain.

4. The method of claim 1 wherein the vagus nerve is indirectly stimulated.

5. The method of claim 4 wherein the vagus nerve is indirectly stimulated with a transdermal or trans-esophageal device.

6. The method of claim 1 wherein the vagus nerve is directly stimulated.

7. The method of claim 6 wherein the vagus nerve is stimulated electrically.

8. The method of claim 6 wherein the efferent vagus nerve is stimulated.

9. The method of claim 8 wherein the efferent vagus nerve is stimulated electrically.

10. The method of claim 6 wherein the vagus nerve is directly stimulated with an implanted device.

11. The method of claim 1 wherein the subject suffers from a condition of hemophilia.

12. The method of claim 1 wherein the subject is suffering from a clotting disorder other than hemophilia.

13. The method of claim 1 wherein the subject is suffering bleeding caused by a wound.

14. The method of claim 1 wherein the subject is undergoing surgery.

15. A method of reducing bleed time in a subject expected to suffer bleeding during a surgical procedure, the method comprising activating the cholinergic anti-inflammatory pathway by stimulating the vagus nerve with a signal current of less than 10 mA, wherein the cholinergic anti-inflammatory pathway is stimulated prior to the surgical procedure; performing the surgical procedure; and reducing bleeding that resulted from the surgical procedure by at least 20%.

16. A method of reducing bleed time in a subject suffering bleeding, the method comprising activating the cholinergic anti-inflammatory pathway by stimulating the vagus nerve with a constant voltage of between about 0.01V to 10V; and reducing bleed time of the bleeding by at least 20%.

17. The method of claim 16 wherein the cholinergic anti-inflammatory pathway is activated by stimulating the vagus nerve with a constant voltage of between about 0.01V to 1V.

18. The method of claim 16 wherein the cholinergic anti-inflammatory pathway is activated by stimulating the vagus nerve with a constant voltage of between about 0.01V to 0.1V.

19. The method of claim 16 wherein the cholinergic anti-inflammatory pathway is activated by stimulating the vagus nerve with a constant voltage of between about 0.01V to 0.05V.

20. A method of reducing bleed time in a subject suffering bleeding, the method comprising activating the cholinergic anti-inflammatory pathway by stimulating the vagus nerve without decreasing the heart rate of the subject; and reducing bleed time of the bleeding by at least 20%.

21. A method of reducing bleed time in a subject in need of such treatment, the method comprising activating the cholinergic anti-inflammatory pathway by stimulating the vagus nerve; and reducing bleed time of the bleeding by at least 20%, wherein the subject is suffering bleeding caused by a wound.

22. The method of claim 1 wherein the activating includes stimulating for about 20 minutes or less.

23. The method of claim 1 wherein the activating includes stimulating for about 1 to about 120 seconds.

24. The method of claim 1, wherein the bleed time is reduced by at least 70% over non-treated controls.

* * * * *

UNITED STATES PATENT AND TRADEMARK OFFICE
CERTIFICATE OF CORRECTION

PATENT NO. : 8,729,129 B2  
APPLICATION NO. : 11/088683  
DATED : May 20, 2014  
INVENTOR(S) : Kevin J. Tracey et al.

Page 1 of 1

It is certified that error appears in the above-identified patent and that said Letters Patent is hereby corrected as shown below:

In the Specification

Column 7, line 18: after "nicotinic agonist is", please delete "(-)-spiro[1'-azabicyclo" and insert --(-)-spiro[1-azabicyclo--.

Column 11, line 2: after "naphthalene-2-sulfonate," and before "and the like.", delete "mandelatek," and insert --mandelate,--.

Column 12, line 39: before "and amiodarone)", delete "AMSH," and insert --αMSH,--.

Signed and Sealed this  
Seventeenth Day of March, 2015

Michelle K. Lee  
*Director of the United States Patent and Trademark Office*